(12) United States Patent
Rupcich et al.

(10) Patent No.: US 10,973,489 B2
(45) Date of Patent: Apr. 13, 2021

(54) CT IMAGING SYSTEM AND METHOD USING A TASK-BASED IMAGE QUALITY METRIC TO ACHIEVE A DESIRED IMAGE QUALITY

(71) Applicant: General Electric Company, Schenectady, NY (US)

(72) Inventors: Franco Rupcich, Wauwatosa, WI (US); Dominic Crotty, Waukesha, WI (US); Jiahua Fan, New Berlin, WI (US); Parag Khobragade, Milwaukee, WI (US); Tal Gilat Schmidt, Milwaukee, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 16/020,385

(22) Filed: Jun. 27, 2018

(65) Prior Publication Data

US 2019/0099148 A1 Apr. 4, 2019

Related U.S. Application Data

(60) Provisional application No. 62/565,662, filed on Sep. 29, 2017.

(51) Int. Cl.
*A61B 6/03* (2006.01)
*H05G 1/08* (2006.01)
(Continued)

(52) U.S. Cl.
CPC .............. *A61B 6/545* (2013.01); *A61B 6/032* (2013.01); *A61B 6/035* (2013.01); *A61B 6/40* (2013.01);
(Continued)

(58) Field of Classification Search
CPC ............ H05G 1/26; H05G 1/265; H05G 1/30; H05G 1/32; H05G 1/34; H05G 1/46;
(Continued)

(56) References Cited

U.S. PATENT DOCUMENTS

| | | | | |
|---|---|---|---|---|
| 5,166,961 A | * | 11/1992 | Brunnett | A61B 6/032 378/116 |
| 5,379,333 A | * | 1/1995 | Toth | A61B 6/032 378/108 |

(Continued)

FOREIGN PATENT DOCUMENTS

| | | |
|---|---|---|
| JP | 2007-289699 A | 11/2007 |
| JP | 2012-90887 A | 5/2012 |

(Continued)

OTHER PUBLICATIONS

Samei et. al., "Assessment of the Dose Reduction Potential of a Model-Based Iterative Reconstruction Algorithm using a Task-Based Performance Metrology" Medical Physics 42(1); (2015) 12 pages.

(Continued)

*Primary Examiner* — Allen C. Ho
(74) *Attorney, Agent, or Firm* — The Small Patent Law Group LLC; Dean D. Small

(57) ABSTRACT

Computed tomography (CT) imaging system has at least one processing unit configured to receive operator inputs that include a modified system feature and a clinical task having a task object and also receive operator inputs for determining a task-based image quality (IQ) metric. The task-based IQ metric represents a desired overall image quality of image data for performing the clinical task. The image data acquired using a reference system feature. The at least one processing unit is also configured to determine an exposure-control parameter based on the task object, the modified system feature, and the task-based IQ metric. The at least (Continued)

one processing unit is also configured to direct the x-ray source to generate the x-ray beam during the CT scan, wherein at least one of the tube current or the tube potential during the CT scan is a function of the exposure-control parameter.

20 Claims, 5 Drawing Sheets

(51) Int. Cl.

| | | |
|---|---|---|
| H05G 1/26 | (2006.01) | |
| H05G 1/30 | (2006.01) | |
| H05G 1/32 | (2006.01) | |
| H05G 1/34 | (2006.01) | |
| H05G 1/46 | (2006.01) | |
| A61B 6/00 | (2006.01) | |

(52) U.S. Cl.
CPC .............. *A61B 6/44* (2013.01); *A61B 6/4429* (2013.01); *A61B 6/4435* (2013.01); *A61B 6/46* (2013.01); *A61B 6/488* (2013.01); *A61B 6/5258* (2013.01); *A61B 6/5294* (2013.01); *A61B 6/54* (2013.01); *A61B 6/542* (2013.01); *A61B 6/544* (2013.01); *H05G 1/08* (2013.01); *H05G 1/26* (2013.01); *H05G 1/265* (2013.01); *H05G 1/30* (2013.01); *H05G 1/32* (2013.01); *H05G 1/34* (2013.01); *H05G 1/46* (2013.01); *A61B 6/467* (2013.01)

(58) Field of Classification Search
CPC .......... H05G 1/08; A61B 6/032; A61B 6/035; A61B 6/44; A61B 6/4429; A61B 6/4435; A61B 6/488; A61B 6/52; A61B 6/5258; A61B 6/5294; A61B 6/54; A61B 6/542; A61B 6/544; A61B 6/545; A61B 6/46; A61B 6/467; A61B 6/469; A61B 6/40
USPC ....... 378/16, 62, 98.7, 98.9, 98.11, 108–112, 378/15
See application file for complete search history.

(56) References Cited

U.S. PATENT DOCUMENTS

| | | | | |
|---|---|---|---|---|
| 5,400,378 A * | 3/1995 | Toth | ................ | A61B 6/032 378/108 |
| 5,450,462 A * | 9/1995 | Toth | ................ | A61B 6/032 378/108 |
| 5,485,494 A * | 1/1996 | Williams | ................ | A61B 6/032 378/110 |
| 5,625,662 A * | 4/1997 | Toth | ................ | H05G 1/26 378/108 |
| 5,696,807 A * | 12/1997 | Hsieh | ................ | A61B 6/032 378/109 |
| 5,822,393 A * | 10/1998 | Popescu | ................ | A61B 6/032 378/108 |
| 5,867,555 A * | 2/1999 | Popescu | ................ | A61B 6/032 378/16 |
| 5,949,811 A * | 9/1999 | Baba | ................ | A61B 6/4225 378/108 |
| 6,047,042 A * | 4/2000 | Khutoryansky | ....... | G01N 23/04 378/62 |
| 6,094,468 A * | 7/2000 | Wilting | ................ | A61B 6/032 378/16 |
| 6,385,280 B1 * | 5/2002 | Bittl | ................ | A61B 6/032 378/106 |
| 6,404,844 B1 * | 6/2002 | Horiuchi | ................ | A61B 6/032 378/16 |
| 6,490,337 B1 * | 12/2002 | Nagaoka | ................ | A61B 6/032 378/16 |
| 6,507,639 B1 * | 1/2003 | Popescu | ................ | A61B 6/032 378/108 |
| 6,744,846 B2 * | 6/2004 | Popescu | ................ | A61B 6/032 378/16 |
| 6,754,301 B2 * | 6/2004 | Horiuchi | ................ | A61B 6/032 378/16 |
| 6,842,502 B2 * | 1/2005 | Jaffray | ................ | A61B 6/466 378/65 |
| 6,850,588 B2 * | 2/2005 | Arenson | ................ | A61B 6/107 378/108 |
| 6,870,898 B1 * | 3/2005 | von der Haar | ........ | A61B 6/032 378/97 |
| 6,904,127 B2 * | 6/2005 | Toth | ................ | A61B 6/032 378/108 |
| 6,956,929 B2 * | 10/2005 | Wolf | ................ | A61B 6/032 378/109 |
| 6,987,828 B2 * | 1/2006 | Horiuchi | ................ | G01N 23/046 378/108 |
| 6,990,171 B2 * | 1/2006 | Toth | ................ | A61B 6/032 378/158 |
| 6,990,172 B2 * | 1/2006 | Toth | ................ | A61B 6/032 378/109 |
| 7,039,163 B2 * | 5/2006 | Popescu | ................ | A61B 6/032 378/109 |
| 7,042,977 B2 * | 5/2006 | Dafni | ................ | A61B 6/032 378/16 |
| 7,068,750 B2 * | 6/2006 | Toth | ................ | A61B 6/032 378/156 |
| 7,082,183 B2 * | 7/2006 | Toth | ................ | A61B 6/032 378/16 |
| 7,103,139 B2 * | 9/2006 | Nagaoka | ................ | A61B 6/032 378/16 |
| 7,106,824 B2 * | 9/2006 | Kazama | ................ | A61B 6/032 378/110 |
| 7,142,630 B2 * | 11/2006 | Suzuki | ................ | A61B 6/032 378/16 |
| 7,145,982 B2 * | 12/2006 | Ikeda | ................ | A61B 6/032 378/16 |
| 7,203,270 B2 * | 4/2007 | Okumura | ................ | A61B 6/032 378/109 |
| 7,209,537 B2 * | 4/2007 | Popescu | ................ | A61B 6/032 378/108 |
| 7,215,733 B2 * | 5/2007 | Nabatame | ................ | A61B 6/032 378/110 |
| 7,272,207 B1 * | 9/2007 | Aufrichtig | ............ | A61B 6/032 378/116 |
| 7,280,635 B2 * | 10/2007 | Toth | ................ | A61B 6/032 378/108 |
| 7,336,762 B2 * | 2/2008 | Seto | ................ | A61B 6/032 378/110 |
| 7,352,840 B1 * | 4/2008 | Nagarkar | ................ | A61B 6/032 250/363.02 |
| 7,391,843 B2 * | 6/2008 | Toth | ................ | A61B 6/488 378/16 |
| 7,460,635 B2 * | 12/2008 | Fujimoto | ................ | A61B 6/032 378/16 |
| 7,480,365 B1 | 1/2009 | Topfer et al. | | |
| 7,558,365 B2 * | 7/2009 | Wang | ................ | A61B 6/032 378/16 |
| 7,587,023 B2 * | 9/2009 | Hur | ................ | A61B 6/481 378/110 |
| 7,602,880 B2 * | 10/2009 | Hirokawa | ................ | A61B 6/032 378/108 |
| 7,636,416 B2 * | 12/2009 | Miyazaki | ................ | A61B 6/542 378/108 |
| 7,639,776 B2 * | 12/2009 | Gohno | ................ | A61B 6/032 378/109 |
| 7,711,082 B2 * | 5/2010 | Fujimoto | ................ | A61B 6/032 378/115 |
| 7,715,522 B2 * | 5/2010 | Goto | ................ | A61B 6/032 378/16 |
| 7,734,006 B2 * | 6/2010 | Miyazaki | ................ | A61B 6/542 378/101 |
| 7,756,243 B2 * | 7/2010 | Gohno | ................ | A61B 6/032 378/16 |

(56) References Cited

U.S. PATENT DOCUMENTS

| | | | | |
|---|---|---|---|---|
| 7,778,381 B2* | 8/2010 | Nishide | A61B 6/032 378/109 |
| 7,945,013 B2* | 5/2011 | Goto | A61B 5/4869 378/16 |
| 7,970,098 B2* | 6/2011 | Haras | A61B 6/545 378/16 |
| 7,983,457 B2* | 7/2011 | Toth | A61B 6/032 378/16 |
| 7,995,703 B2* | 8/2011 | Yan | A61B 6/588 378/16 |
| 8,000,510 B2* | 8/2011 | Boeing | A61B 6/545 382/128 |
| 8,031,831 B2* | 10/2011 | Zou | A61B 6/032 378/108 |
| 8,175,217 B2* | 5/2012 | Sugaya | A61B 6/032 378/16 |
| 8,184,768 B2* | 5/2012 | Honda | A61B 6/032 378/134 |
| 8,229,059 B2* | 7/2012 | Mukumoto | A61B 6/032 378/112 |
| 8,699,658 B2* | 4/2014 | Yu | A61B 6/032 378/16 |
| 8,705,695 B2* | 4/2014 | Jabri | A61B 6/542 378/62 |
| 8,718,343 B2* | 5/2014 | Bruder | A61B 6/032 382/131 |
| 8,744,040 B2* | 6/2014 | Sugaya | A61B 6/032 378/16 |
| 8,891,849 B2* | 11/2014 | Rohler | A61B 6/032 382/132 |
| 9,020,220 B2* | 4/2015 | Nukui | A61B 6/542 382/128 |
| 9,036,771 B2* | 5/2015 | Yu | A61B 6/5258 378/19 |
| 9,192,349 B2* | 11/2015 | Haras | G06Q 30/0207 |
| 9,642,588 B2* | 5/2017 | Goto | A61B 6/542 |
| 9,681,851 B2* | 6/2017 | Rohler | A61B 6/032 |
| 9,730,669 B2* | 8/2017 | Lee | A61B 6/545 |
| 9,848,847 B2* | 12/2017 | Boedeker | A61B 6/544 |
| 9,895,128 B2* | 2/2018 | Takahashi | A61B 6/032 |
| 9,936,924 B2* | 4/2018 | Stayman | A61B 6/032 |
| 9,949,711 B2* | 4/2018 | Goto | A61B 6/542 |
| 9,980,690 B2* | 5/2018 | Muroi | A61B 6/463 |
| 9,992,854 B2* | 6/2018 | Allmendinger | A61B 6/4007 |
| 10,034,652 B2* | 7/2018 | Cho | A61B 6/4241 |
| 10,085,698 B2* | 10/2018 | Fan | A61B 6/032 |
| 10,105,118 B2* | 10/2018 | Jung | A61B 6/542 |
| 10,111,626 B2* | 10/2018 | Goto | A61B 6/032 |
| 10,238,357 B2* | 3/2019 | Tanaka | A61B 6/027 |
| 10,265,044 B2* | 4/2019 | Profio | G06T 11/008 |
| 10,278,666 B2* | 5/2019 | Eronen | A61B 6/14 |
| 10,357,215 B2* | 7/2019 | Lee | A61B 6/032 |
| 10,368,825 B2* | 8/2019 | Crotty | A61B 6/542 |
| 10,470,733 B2* | 11/2019 | Goto | A61B 6/4035 |
| 10,524,758 B2* | 1/2020 | Jan | A61B 6/405 |
| 10,667,767 B2* | 6/2020 | Stevens | A61B 6/035 |
| 2007/0258559 A1 | 11/2007 | Hur | |
| 2013/0156151 A1 | 6/2013 | Sugaya | |
| 2013/0243300 A1 | 9/2013 | Oda | |
| 2014/0072108 A1 | 3/2014 | Rohler et al. | |
| 2015/0199478 A1 | 7/2015 | Bhatia | |
| 2016/0042499 A1 | 2/2016 | Dhanantwari | |
| 2016/0253443 A1 | 9/2016 | Li et al. | |
| 2016/0296196 A1 | 10/2016 | Boedeker | |
| 2018/0038969 A1 | 2/2018 | McCloolugh et al. | |

FOREIGN PATENT DOCUMENTS

| | | |
|---|---|---|
| JP | 2013-192697 | 9/2013 |
| JP | 2016-514614 A | 5/2016 |
| JP | 2016-198501 A | 12/2016 |
| JP | 2017-501787 A | 1/2017 |
| WO | 2012/033028 | 3/2012 |

OTHER PUBLICATIONS

Chen et. al., "Assessment of Volumetric Noise and Resolution Performance for Linear and Nonlinear CT Reconstruction Methods" Med Phys, vol. 41 (2014) 14 pages.

Gang et. al.,"Analysis of Fourier-domain task-based detectability index in tomosynthesis and cone-beam CT in relation to human observer performance." Medical physics 38.4: 1(2011) 754-1768.

Kaza et al., "Emerging Techniques for Dose Optimization in Abdominal CT" Radio Graphics, vol. 34, No. 1; (2014) 15 pages.

Mccollough et al., "CT Dose Reduction and Dose Management Tools: Overview of Available Options" Radio Graphics; vol. 26, No. 2; (2006) 11 pages.

Raman et al., "CT Dose Reduction Applications: Available Tools on the Latest Generation of CT Scanners" Journal of the American College of Radiology; vol. 10, No. 1; (2013) 5 pages).

Yu et al., "Optimal Tube Potential for Radiation Dose Reduction in Pediatric CT: Principles, Clinical Implementation, and Pitfalls" Radio Graphics; vol. 31, No. 3 (2001) 15 pages.

Soderberg et al., "Aytomatic Exposure Control in Computed Tomography—An Evaluation of Systems from Different Manufacturers" ACTA Radiologica 51:6; (2010) 11 pages.

Japanese Pat. Appl. No. 2018-170144, Notice of Reasons for Refusal, dated Jan. 7, 2020 (with translation, 10 pages total).

Japanese Pat. Appl. No. 2018-170144, Notice of Reasons for Refusal, dated Jun. 10, 2020 (with translation, 8 pages total).

Japanese Pat. Appl. No. 2018-170144, Decision to Grant a Patent, dated Oct. 14, 2020 (with translation, 5 pages total).

* cited by examiner

CT IMAGING SYSTEM AND METHOD USING A TASK-BASED IMAGE QUALITY METRIC TO ACHIEVE A DESIRED IMAGE QUALITY

CROSS-REFERENCE TO RELATED APPLICATION

The present application claims the benefit of U.S. Provisional Application No. 62/565,662, which was filed on Sep. 29, 2017 and is incorporated herein by reference in its entirety.

FIELD

The subject matter disclosed herein relates generally to medical imaging systems.

BACKGROUND

Computed tomography (CT) imaging systems are typically controlled by trained operators that select a number of imaging and/or acquisition parameters that prescribe a CT scan. These parameters may be selected based on, among other things, the region-of-interest (ROI) and the clinical task. Clinical tasks may include, for example, detecting and characterizing nodules in the body, identifying an abnormal collection of fluid (gas or liquid), characterizing conditions of soft tissue, or identifying an abnormal congenital or developed anatomy of the person. Medical images with better image quality are generally easier to read for accomplishing the clinical task. But for certain medical imaging systems, such as CT imaging systems, acquiring medical images with better image quality may require exposing the person to a greater amount of radiation. Thus, one challenge for operators of CT imaging systems is to obtain medical images having a sufficient image quality without subjecting the person to unnecessary radiation.

Image quality, however, can be a function of several factors, including noise, contrast, spatial resolution, and/or noise texture. Each of these factors can be influenced by one or more adjustable parameters of the CT imaging system. To assist the operator in achieving sufficient image quality, manufacturers have developed several features, such as automated control systems that automatically adjust operation of the imaging system.

The adjustments made by the automated control system may be based on parameters entered by the operator. For example, automatic exposure control (AEC) engines in CT imaging systems may modulate a radiation dose based on an image quality (IQ) reference entered by the operator. To modulate the radiation dose, the AEC engine may modulate tube current and/or tube potential (or tube voltage). The IQ reference is indicative of an image quality desired by the operator. For example, the IQ reference may specify a minimum acceptable image quality for the resulting image data. The IQ reference may be, for example, a noise index that is directly proportional to image noise and represents an acceptable amount of noise that can be present in the medical images the operator would like to acquire. The AEC engine attempts to modulate the tube current to achieve constant image noise regardless of the attenuation level. Other IQ references entered by operators may be a reference mAs that is directly proportional to a tube current-time product, a reference image having an acceptable image quality, and a target image quality level based on a standard deviation of pixel values in an image.

Operators often desire to improve a protocol (e.g., by reducing dosage) without reducing image quality to which the operator is accustomed. While attempting to improve the protocol, the operator may enter the same IQ reference while changing one or more scan parameters or changing the reconstruction technique. In such instances, the AEC engines may not sufficiently account for how the modifications affect the overall image quality. For example, the known AEC engine that uses a noise index may be able to maintain equivalent noise between different protocols, but noise alone may not preserve the "look and feel" of an image. The overall image quality is based not only on noise but other factors, such as contrast, spatial resolution, and/or noise texture. Limitations to the known IQ references may be especially noticeable when changing the reconstruction kernel, changing a reconstructive technique, varying the level (or strength) of iterative reconstruction, or changing a tube potential (kV).

Accordingly, it can be difficult and time-consuming for an operator to develop a new protocol that achieves a desired image quality for a designated clinical task. Moreover, as discussed above, conventional IQ references may be insufficient when using a different reconstruction algorithm or when using a modified scan parameter in a scan prescription.

BRIEF DESCRIPTION

In one or more embodiments, a computed tomography (CT) imaging system is provided that includes an x-ray source configured to operate at a tube current and at a tube potential while generating an x-ray beam. The CT imaging system also includes a CT detector configured to collect projection data of a person and at least one processing unit configured to execute programmed instructions stored in memory. The at least one processing unit, when executing the programmed instructions, is configured to receive operator inputs that include a modified system feature and a clinical task having a task object. The at least one processing unit is also configured to receive operator inputs for determining a task-based image quality (IQ) metric. The task-based IQ metric represents a desired overall image quality of image data for performing the clinical task. The image data acquired using a reference system feature. The reference system feature and the modified system feature are the same type of feature. The at least one processing unit is also configured to determine an exposure-control parameter based on the task object, the modified system feature, and the task-based IQ metric. The at least one processing unit is also configured to direct the x-ray source to generate the x-ray beam during the CT scan, wherein at least one of the tube current or the tube potential during the CT scan is a function of the exposure-control parameter.

In some aspects, the reference system feature and the modified system feature are a reconstruction algorithm or a scan parameter.

In some aspects, the at least one processing unit includes an automatic exposure control (AEC) engine that is configured to receive the exposure-control parameter and direct the x-ray source to generate the x-ray beam based on the exposure-control parameter.

In some aspects, the AEC engine determines a tube-current modulation (TCM) profile using the exposure-control parameter. The TCM profile specifies tube currents during the CT scan for different angular and longitudinal positions of the x-ray source. The at least one processing unit is configured to direct the x-ray source to generate the x-ray beam according to the TCM profile.

In some aspects, determining the exposure-control parameter includes determining at least one weighting factor. The at least one weighting factor is based on the task object and the reconstruction algorithm. Additionally, determining the exposure-control parameter includes calculating the exposure-control parameter using the at least one weighting factor and the task-based IQ metric In some aspects, the at least one processing unit includes an automatic exposure control (AEC) engine that is configured to direct the x-ray source to generate the x-ray beam. The exposure-control parameter has a designated relationship with respect to at least one of image noise or a radiation dose parameter. The method also includes converting the exposure-control parameter to a different exposure-control parameter that is configured to be received by the AEC engine.

In some aspects, the task-based IQ metric is determined using a detectability index. The detectability index is a task-based, frequency-dependent signal-to-noise ratio (SNR) metric that combines the spatial resolution (MTF) and noise properties (NPS) of the CT imaging system and spatial-frequency content of the task object. Optionally, the IQ reference includes at least one of a noise standard deviation or a reference tube-current product.

In some aspects, the operator inputs that are received for determining the task-based IQ metric include a reference image having a desired overall image quality. The at least one processing unit, when executing the programmed instructions, is configured to determine the task-based IQ metric using the reference image. Optionally, the task-based IQ metric is a function of at least one of a noise, contrast, or noise texture of the reference image.

In one or more embodiments, a method is provided that includes receiving operator inputs that include a modified system feature and a clinical task having a task object. The method also includes receiving operator inputs for determining a task-based image quality (IQ) metric. The task-based IQ metric represents a desired overall image quality of image data for performing the clinical task. The image data is acquired using a reference system feature, wherein the reference system feature and the modified system feature are the same type of feature. The method also includes determining an exposure-control parameter based on the task object, the modified system feature, and the task-based IQ metric. The method also includes directing the x-ray source to generate the x-ray beam during the CT scan, wherein at least one of the tube current or the tube potential during the CT scan is a function of the exposure-control parameter.

In some aspects, the reference system feature and the modified system feature are a reconstruction algorithm or a scan parameter.

In some aspects, determining the exposure-control parameter includes determining at least one weighting factor, the at least one weighting factor being based on the task object and the reconstruction algorithm, and calculating the exposure-control parameter using the at least one weighting factor and the task-based IQ metric.

In some aspects, the operator inputs received for determining the task-based IQ metric include at least one of a numerical value or a reference image having a desired overall image quality. The exposure-control parameter is based on the task-based quality metric, a modulation transfer function (MTF) for the clinical task, a noise power spectrum (NPS), and a frequency content (W) for the clinical task.

In some aspects, the task-based IQ metric is obtained by a first CT imaging system. The reference system feature is used by the first CT imaging system, wherein the modified system feature is configured to be used by a second CT imaging system and wherein determining the exposure-control parameter includes determining the exposure-control parameter for the second CT imaging system.

In one or more embodiments, a computed tomography (CT) imaging system is provided that includes an x-ray source configured to operate at a tube current and at a tube potential while generating an x-ray beam. The CT imaging system also includes a CT detector configured to collect projection data of a person and at least one processing unit configured to execute programmed instructions stored in memory. The at least one processing unit, when executing the programmed instructions, is configured to receiving operator inputs that include a clinical task having task object, a reference system feature, a modified system feature, and a target image quality (IQ) reference. The reference system feature and the modified system feature are the same type of feature. The target IQ reference represents an acceptable image quality obtainable using the reference system feature. The at least one processing unit is also configured to determine a task-based IQ metric based on the task object, the reference system feature, and the target IQ reference. The at least one processing unit is also configured to determine an adjusted IQ reference based on the task-based IQ metric, the task object, and the modified system feature. The at least one processing unit is also configured to direct the x-ray source to generate the x-ray beam during the CT scan, wherein at least one of the tube current or the tube potential during the CT scan is a function of the adjusted IQ reference.

In some aspects, the at least one processing unit includes an automatic exposure control (AEC) engine that is configured to receive the adjusted IQ reference and direct the x-ray source to generate the x-ray beam based on the adjusted IQ reference.

In some aspects, the AEC engine determines a tube-current modulation (TCM) profile using the adjusted IQ reference, the TCM profile prescribing respective tube currents during the CT scan for different angular and longitudinal positions of the x-ray source, wherein directing the x-ray source to generate the x-ray beam includes directing the x-ray source to generate the x-ray beam according to the TCM profile.

In some aspects, the reference system feature and the modified system feature are either (a) different reconstruction algorithms or (b) different tube potentials.

Optionally, the reconstruction algorithm of the modified system feature includes an iterative reconstruction technique.

In some aspects, the target IQ reference includes at least one of (a) a noise index representing a relative amount of noise within a medical image; (b) a reference medical image having a desired image quality; or (c) a reference mAs representing a tube current-time product divided by a spiral pitch value.

In some aspects, the adjusted IQ reference is based on a modulation transfer function (MTF) for the clinical task, a noise power spectrum (NPS), and a frequency content (W) for the clinical task.

In one or more embodiments, a method is provided that includes receiving operator inputs that include a clinical task having task object, a reference system feature, a modified system feature, and a target image quality (IQ) reference. The target IQ reference represents an acceptable image quality obtainable using the reference system feature. The reference system feature and the modified system feature are the same type of feature. The method may also include determining a task-based IQ metric based on the task object, the reference system feature, and the target IQ reference. The method may also include determining an adjusted IQ reference based on the task-based IQ metric, the task object, and the modified system feature. The method may also include directing the x-ray source to generate the x-ray beam during the CT scan, wherein at least one of the tube current or the tube potential during the CT scan is a function of the adjusted IQ reference.

In some aspects, the reference system feature and the modified system feature and include a reconstruction algorithm or a scan parameter.

BRIEF DESCRIPTION OF THE DRAWINGS

The inventive subject matter described herein will be better understood from reading the following description of non-limiting embodiments, with reference to the attached drawings, wherein below.

DETAILED DESCRIPTION

Figure 1:
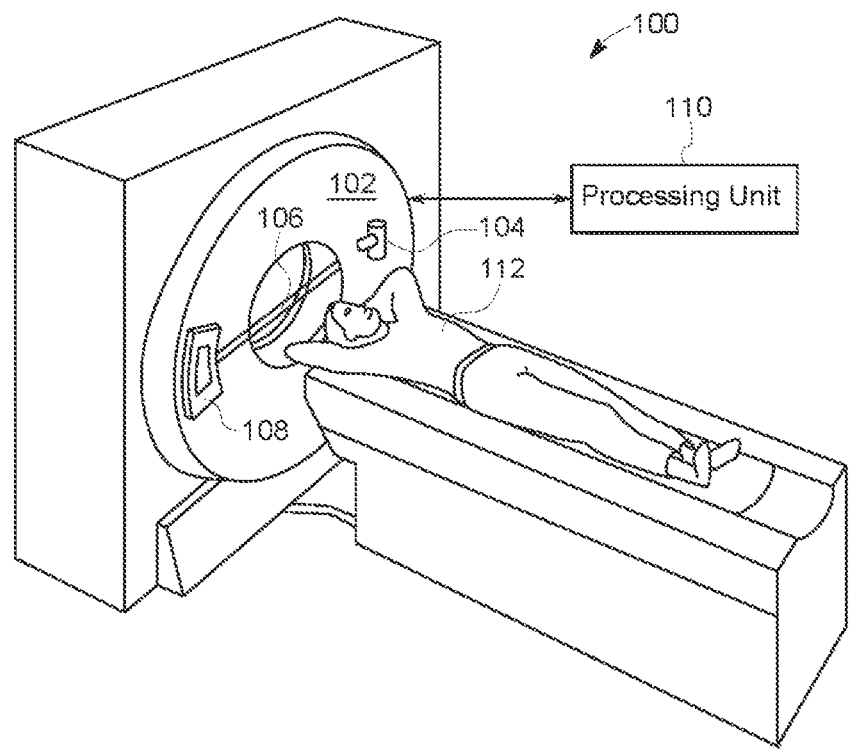
FIG. 1 illustrates a computed tomography (CT) imaging system in accordance with one embodiment.

Embodiments set forth herein may calculate and/or utilize a task-based image quality (IQ) metric in order to generate image data having a desired overall image quality. The task-based IQ metric may be determined (e.g., calculated) using a detectability index. The detectability index may be a task-based, frequency-dependent signal-to-noise ratio (SNR) metric that combines spatial resolution (e.g., modulation transfer function (MTF)) and noise properties (e.g., noise power spectrum (NPS)) of a CT imaging system and spatial-frequency content of a task object. In particular embodiments, the task-based IQ metric is derived from a non-prewhitening detectability index. The task-based IQ metric may be labeled or referred to as "d'" or "d'$_{gen}$" in the description and claims.

Embodiments may enable development of a new protocol that achieves a desired image quality for a designated clinical task. For example, embodiments may enable development of a new protocol that is based on one or more changes to a reference protocol. In particular, the task-based IQ metric may be used to obtain an image quality for the image data generated from the new protocol that is essentially equal to an image quality for the image data of the reference protocol. After a new protocol is performed, an operator may, if desired, store the new protocol with the CT imaging system.

Unlike known IQ references that are used by CT imaging systems, the task-based IQ metric may account for not only noise but also account for other image characteristics, such as contrast, spatial resolution, or noise texture. Moreover, the task-based IQ metric may be configured to be used with a number of different reconstruction algorithms, including iterative reconstruction algorithms. Iterative reconstruction algorithms may have resolution and noise texture properties that can degrade perceived image quality. Alternatively or in addition to reconstruction algorithms, the task-based IQ metric may be configured to be used with a scan parameter that affects at least one of a radiation dose caused by the x-ray source or an image quality of the resulting image data.

Operators of CT imaging systems often enter a target IQ reference into the CT imaging system to specify a minimum acceptable image quality for the resulting image data. The task-based IQ metric described herein may be used to calculate an adjusted IQ reference. In certain embodiments, the IQ reference may be a noise index that represents an acceptable amount of noise present in the image data. In other embodiments, the IQ reference may be a tube current-time product value, a reference image having an acceptable image quality, or a desired standard deviation of pixel values for reconstructed images. An IQ reference, including the IQ references listed above, may be related to image noise in the image data. For example, the IQ reference may have a linear or non-linear relationship with respect to the image noise.

In some cases, however, IQ references may not account for certain image quality characteristics, such as contrast, spatial resolution, or noise texture, all of which may be clinically important when assessing task-based IQ. Accordingly, the task-based IQ metric may be used to modify the target IQ reference. For example, the operator may input a clinical task and a target IQ reference (e.g., desired noise index, reference mAs, reference image, or reference standard deviation). The clinical task may be to identify certain objects in the body. As such, a clinical task may have a task object that is defined by one or more qualities, such as size, shape, and contrast. The target IQ reference may correspond to an acceptable image quality that the operator is accustomed to for a designated clinical task. The target IQ reference may be based on a commercial standard that was developed using a conventional reconstruction algorithm, such as a filtered backprojection (FBP), or using a common value for a scan parameter (e.g., 120 kV).

The operator may also input a reconstruction algorithm or a scan parameter that affects the radiation output and/or the image quality. The reconstruction algorithm or the scan parameter may differ from the reconstruction algorithm or the scan parameter, respectively, that the operator is accustomed to for the clinical task. Due to these changes, the target IQ reference that the operator would typically enter for the clinical task may not generate image data having the desired image quality. In such instances, embodiments may use the task-based IQ metric to adjust the target IQ reference and then provide the adjusted target IQ reference (called "adjusted IQ reference") to an automatic exposure control (AEC) engine. The adjusted IQ reference will cause the AEC engine to provide a different radiation output compared to the radiation output that would be provided using the target IQ reference.

The adjusted IQ reference may be the same as or similar to an "exposure-control parameter." Like the adjusted IQ reference, the exposure-control parameter may be provided as an input to the AEC engine, and the AEC engine may use the input to determine the radiation output (or radiation dose) provided by the CT imaging system. For example, an adjusted IQ reference may be converted to an exposure-control parameter. Alternatively, the exposure-control parameter may be the adjusted IQ reference without modification.

The AEC engine may use the adjusted IQ reference or the exposure-control parameter to generate a tube-current modulation (TCM) profile. The TCM profile may include a tube current and/or a tube potential for each position of the x-ray source. Each position of the x-ray source during the CT scan may be a function of an angular/rotational orientation of the x-ray source (or CT detector) and a Z location of the x-ray source (or the CT detector). The tube potential may change less frequently than the tube current. In some cases, the tube potential is selected prior to the CT scan and is not changed during the CT scan.

The TCM profile may be generated using the adjusted IQ reference (or exposure-control parameter) and patient attenuation information. The tube current for achieving the prescribed image noise, which is based on the IQ reference, may be calculated using known x-ray physics relationships. Image noise is inversely related to the number of photons and the number of photons is related to the slice thickness, image acquisition time, and tube current. Accordingly, a tube current may be determined for various positions and orientations of the x-ray source during the CT scan. Adjustment factors may also be applied to account for certain variables, such as helical pitch.

As used herein, a "system feature" includes a reconstruction algorithm or a scan parameter (e.g., kV, gantry rotation speed, pitch) that affects at least one of a radiation output or image quality. When changed by the operator, the system feature, the scan parameter, or the reconstruction algorithm may be referred to as the "modified system feature," "modified scan parameter," or the "modified reconstruction algorithm." As described herein, an IQ reference may have been developed using predetermined system features or developed for use with the predetermined system features. For example, a table of noise indexes may have been developed in which the expected reconstruction algorithm when using the noise indexes is FBP. In this instance, the system feature, the scan parameter, or the reconstruction algorithm may be referred to as the "reference system feature," "reference scan parameter," or the "reference reconstruction algorithm."

A reference system feature and a modified system feature may be the "same type" of feature if, for example, the reference system feature and the modified system feature may replace each other for a CT scan. For example, a FBP algorithm may be replaced by an iterative algorithm without providing a defective or inoperable scan prescription. As another example, 80 kV for a tube potential value may be replaced by 110 kV. In addition to tube potentials, other types of scan parameter that may be modified include a tube current product (mAs), a gantry tilt, a gantry rotation time or speed, a helical pitch, a slice thickness, and a relative movement of the x-ray source and the CT detector along the z-axis.

The IQ reference may be a standardized metric or parameter that operators have become accustomed to when requesting a desired image quality. For example, the noise index was developed using FBP reconstructed image data and/or with FBP as the intended reconstruction algorithm of the image data. If the modified system feature provided by the operator is a different reconstruction algorithm (e.g., iterative reconstruction algorithm), then the resulting image data may have an image quality that is less than desired or may have an image quality that is greater than desired. If the image quality is greater than desired, a smaller radiation output could be used to decrease exposure to the person.

The AEC engine may determine a TCM profile for the CT scan using the operator inputs and information from a scout scan. Scout scans may also be referred to as topograms, scanned projection radiographs (SPRs), pilot scans, or localizer scans. Scout scans may have slightly poorer image data than the subsequent diagnostic CT scan. Scout scans provide information for determining a density, a size, and a shape of the person. For example, total projection attenuation may include information relating to a density and a size of the person, and an amplitude and width of the projection from the scout scan may include information relating to a shape of the person. Such information may be used to predict how many x-ray photons will reach the CT detector for a scan prescription and predict a standard deviation due to x-ray noise.

Embodiments can use the task-based IQ metric to adjust the target IQ reference. The AEC engine may then use the adjusted IQ reference to develop the TCM profile. Optionally, the TCM profile based on the adjusted IQ reference may be configured to achieve an image quality that is essentially equivalent to the image quality that was based on the target IQ reference but with a reduced exposure to the patient. Optionally, the TCM profile based on the adjusted IQ reference may be configured to achieve an image quality that is better than the image quality based on the target IQ reference but without increasing exposure to the patient.

To illustrate one particular example, the CT imaging system may receive a target noise index that is entered by the operator. In known CT imaging systems, the system would determine a TCM profile that would generate image data having a noise level that is approximately equal to the noise index. However, the operator may also select a different reconstruction algorithm that the operator is not accustomed to for the clinical task. As discussed above, an IQ reference for a clinical task that generates FBP image data may be incorrect for a clinical task that generates iteratively-reconstructed image data. As described herein, the task-based IQ metric may address this discrepancy by providing an overall image quality for the iteratively-reconstructed image data that is similar to the overall image quality of the FBP image data. In particular, the CT imaging system may use the task-based IQ metric to adjust the target IQ reference and then use the adjusted IQ reference (instead of the originally inputted target IQ reference) to generate the TCM profile.

In some embodiments, the AEC engine may be configured to receive one type of IQ reference. For instances in which an adjusted IQ reference does not match the input to the AEC engine, the adjusted IQ reference or the exposure-control parameter may be converted from one value (e.g., noise index) to another value (e.g., reference mAs). This conversion may be performed using one or more models or indexes (e.g., database or lookup-table). Optionally, the indexes or models may be based on a radiation dose or exposure. Various parameters may be used to characterize the radiation dose or exposure. Radiation dose parameters include, for example, a volume CT dose index ($CTDI_{vol}$, expressed in milligrays), dose length product (DLP, expressed in milligrays-centimeter), and a size-specific dose estimate (SSDE). $CTDI_{vol}$ is a measure of the radiation output from the CT imaging system as determined with a designated phantom (e.g., 16 or 32 cm PMMA phantom). DLP is the $CTDI_{vol}$ multiplied by scan length. SSDE is a measure of dose that includes an individual person size. SSDE is calculated by multiplying the $CTDI_{vol}$ with a correction factor based on a person effective diameter. In some embodiments, the radiation dose parameter may be a function of multiple variables, such as $CTDI_{vol}$, DLP, or SSDE.

Conversion indexes or models for converting the IQ references may be generated through experimentation, simulation, and/or modeling. For example, two different CT imaging systems having AEC engines that receive the two different inputs may perform a CT scan of the same phantom at equal or approximately equal scan prescriptions. The data used by the AEC engine and generated by the CT scans may be used to generate a conversion database or a conversion model.

The AEC engine may direct the x-ray source to modulate the tube current and/or a tube potential to achieve a desired image quality that is prescribed by the operator. It is contemplated that the AEC engine may control one or more other scan parameters, such as a gantry rotation time, a pitch, or an operating or active configuration for the CT detector. The pitch is a ratio of table feed per gantry rotation to a width of the x-ray beam measured along the z-axis.

AEC engines may be preprogrammed and/or operate in near real-time using a feedback mechanism, or both. For example, the AEC engine may develop the TCM profile prior to initiating the CT scan. Tube-current modulation may be based on angular position (in-plane), longitudinal position (z-axis), or a combination of angular and longitudinal positions. In some embodiments, the modulation is temporal (ECG-gated). Optionally, the tube current may be modulated using online feedback (e.g., measurements from previous 180 degree views) or using predictive calculations or sinusoidal interpolations between anterior-posterior and lateral views.

The CT system is configured to operate in accordance with a reference protocol that includes a scan prescription. The scan prescription includes a set of designated system features that determine operation of the CT system (e.g., CT detector and x-ray source) and/or influence output (e.g., type of data generated). System features include scan parameters and reconstruction algorithms, but may also include other parameters, settings, conditions, and/or scanning modes that are selected by the operator or determined by the CT system. In particular embodiments, the system features include scan parameters, which affect the acquired projection data and include, for example, a tube potential (kV) of the x-ray source, a tube current (mA) of the x-ray source, a tube current product (mAs), a gantry tilt, a gantry rotation time or speed, a helical pitch, a slice thickness, and relative movement of the x-ray source and the CT detector along the z-axis. Scanning modes include, for example, axial scanning, helical scanning, high resolution imaging, and material density (spectral) imaging, cardiac scanning, or cine scanning.

An operator or CT imaging system may select a reference protocol. In response to selecting the reference protocol, the CT imaging system may populate values/information for the various parameters, settings, conditions, algorithms, etc. of the scan prescription. In some embodiments, an operator is enabled to modify the scan prescription through operator inputs. For example, the operator inputs may add one or more new parameters or change one or more of the pre-programmed values/information. The new parameters may be, for example, a target IQ reference or a task-based IQ metric.

Reference protocols can be designed for particular clinical tasks. Reference protocols may be selected by the operator or automatically selected by the CT system based on a selected clinical task and, optionally, other factors, such as a person size or age. The scan parameters of the reference protocol may be adjustable by the operator. For example, the reference protocol may include pre-programmed scan parameters, such as a gantry tilt, an interval per rotation or gantry rotation speed, a helical pitch, a slice thickness, a field-of-view, a kV, a mA, and/or an mAs. Other scan parameters may include start and end locations, right-left center, anterior-posterior center, and detector configuration or beam collimation.

The pre-programmed scan parameters of the reference protocol form a proposed scan prescription. In some embodiments, the CT imaging system receives operator inputs that can be used to modify the scan prescription of the reference protocol, thereby generating a modified scan prescription. For example, the operator may provide an IQ reference, such as a noise index or a reference image, that approximates an image quality for the reconstructed images. The AEC engine may automatically adjust the tube current based on the IQ reference and other information. For example, the AEC engine may automatically adjust the tube current to compensate for variations in person attenuation.

A reconstruction algorithm determines how data (e.g., raw projection data or image data) may be processed to generate reconstructed image data. A reconstruction algorithm may be identified by a reconstruction technique (e.g., filtered backprojection (FBP) or iterative reconstruction (IR)) and a reconstruction kernel (e.g., soft tissue, standard, detail, chest, lung, bone, or edge). Reconstruction kernels may affect spatial resolution and low contrast detectability. If applicable, the reconstruction algorithm may also have a level or strength of the reconstruction technique or other characteristic of the reconstruction technique. For instance, a number of iterative loops executed by the iterative reconstruction technique may be controlled. Also, an iterative reconstruction technique may blend iteratively-reconstructed image data with FBP image data. The iteratively-reconstructed image data may contribute 10%, 20%, 30%, 40%, 50%, or more to the resulting image data.

Iterative reconstruction may use a trial-and-error algorithm in which image data is iteratively processed through a series of iterative or correction loops. For the first loop, the projection data is compared to a proposed ideal image and processed to generate image data that is closer to the proposed ideal image. For each loop after the first loop, the image data (e.g., from the preceding loop) is reconstructed and the newly reconstructed image data is compared to a proposed ideal image. If a deviation between the latest reconstructed image and the proposed ideal image does not satisfy the predetermined condition, the reconstructed image data is modified so that the modified reconstructed image data is closer to the proposed ideal image. When a deviation between the latest reconstructed image data and the proposed ideal image satisfies the predetermined condition, the iterative reconstruction process stops. The iterative reconstruction may be performed in the projection space (e.g., with projection data from the CT detector) or in the image space (e.g., after the projection data is processed and reconstructed). For at least some iterative reconstruction algorithms, the corrections loop occur in the projection space and also in the image space.

Different iterative reconstruction algorithms may incorporate different x-ray photon noise statistics and/or system optics modeling. In some embodiments, the iterative reconstruction algorithm may blend image data that was reconstructed using an iterative technique with image data that was generated from another reconstruction technique. For example, iteratively-reconstructed image data may be blended with FBP image data. The amount of blending may be selected by the operator. For instance, the iteratively-reconstructed image data may contribute 10%, 20%, 30%, 40%, 50%, or more to the resulting image data.

Various IQ references exist that are inputted to the AEC engines for determining a radiation output of the x-ray source during the CT scan. The IQ reference approximates an image quality desired by the operator for the resulting image data. The noise index is a measure of a noise level defined relative to a uniform water phantom. A higher noise index means the image data will contain relatively more noise, while a lower noise index means the image data will contain relatively less noise. The operator may also define a range within which the tube current can be modulated by selecting minimum and maximum mA limits. The AEC engine may modulate the tube current along only the z-axis or along each of the x-, y-, and z-axes to maintain an amount of noise in the image data, wherein the amount of noise is based on the noise index.

A reference image may also be used as an IQ reference. The reference image may be selected by the operator or CT imaging system for having a desired image quality for the clinical task. The reference image may be an actual clinical image or an ideal clinical image for the clinical task. The reference image may be analyzed to determine an image quality (e.g., noise or the task-based quality metric described herein) of the reference image. In some embodiments, the AEC engine may modulate the tube current so that X % of the image data (e.g., 90% of the image data) will have a noise equal to or less than that of the reference image. The remaining amount of image data may have a noise equal to or greater than that of the reference image. Alternatively, the AEC engine may modulate the tube current so that X % of the image data (e.g., 90% of the image data) will have an overall image quality that is equal to or less than that of the reference image. The remaining amount of image data may have an overall image quality that is equal to or greater than that of the reference image.

A reference mAs is another IQ reference that may be used by one or more embodiments. The reference mAs is directly proportional to a tube current-time product. For each reference protocol or clinical task, the user selects the effective tube current-time product (or tube current-time product/pitch). For adult protocols, the effective tube current-time product may be used for an adult patient having a designed weight (e.g., approximately 80 kilograms). A tube current-time product corresponds to radiation exposure. For pediatric protocols, the effective tube current-time product may be used for a pediatric patient having a designed weight (e.g., approximately 20 kg). A target noise (or standard deviation of CT numbers) is varied on the basis of patient size by using an empirical algorithm. As such, image noise is not kept constant for all patients and is adjusted according to an empirical impression of image quality. A scout scan of the person is used to predict a TCM profile (with variations along the x-, y-, and z-axes) that will yield the desired image quality, given the size and anatomy of the person. Optionally, an online feedback system may modify the actual tube current during the CT scan to match the patient-specific attenuation values at different angles.

Reference mAs is related to mAs and has a linear relationship with respect to $CTDI_{vol}$. Noise index is related approximately to the inverse of the square root of the effective mAs. The noise index has a nonlinear relationship with respect to the $CTDI_{vol}$. Using $CTDI_{vol}$ as a common parameter, a conversion model or index (e.g., table) may be developed for converting between the noise index and the reference mAs. Similar conversion indexes or models may be generated for converting between other IQ references.

Instead of entering a known IQ reference, the operator may directly enter a task-based IQ metric. Unlike a noise index or other known IQ references, the task-based IQ metric may provide a better representation of overall image quality by accounting for not only noise but also contrast, spatial resolution, and/or noise texture. Embodiments may use the task-based IQ metric to generate a scan prescription for a designated clinical task.

Clinical tasks include using the CT image data to detect and/or characterize certain material within the body to assess a health status of a person. The material may be, for example, nodules, masses, collected fluid, soft tissue having a certain condition, and an abnormal congenital or developed anatomy of the person. In one or more embodiments, the task-based IQ metric is based on qualities of a task object for the clinical task. The task object is the feature sought to be detected by the clinical task and may be a nodule, mass, collected fluid, etc. The qualities of the task object may include, for example, a size of the task object (in millimeters), a shape of the task object (e.g., circular, oval), and a contrast of the task object (e.g., low contrast, medium contrast, high contrast). High contrast may be defined as, for example, above 100 HU.

In some embodiments, at least one technical effect of the subject matter described herein includes an IQ reference (referred to herein as a task-based IQ metric) that provides a better representation of overall image quality compared to other IQ references used by known CT imaging systems. For example, the task-based IQ metric may account for not only noise (like the other IQ references), but also contrast, spatial resolution, and noise texture. In some embodiments, at least one technical effect of the subject matter described herein includes CT imaging systems that are capable of using the task-based IQ metric to provide image data with overall image quality that is closer to the desired overall image quality. In some embodiments, at least one technical effect of the subject matter described herein includes CT imaging systems that are capable of receiving a target IQ reference, which the operator is accustomed to using to obtain a desired image quality, and adjusting the target IQ reference based on a task-based IQ metric for a different scan prescription. For example, the target IQ reference may be associated with a first reconstruction algorithm (e.g., FBP), and the adjusted IQ reference may be for acquiring image data with a different second reconstruction algorithm (e.g., iterative reconstruction). The task-based IQ metric and the adjusted IQ reference may be determined "under the hood" such that the operator may not be aware that the task-based IQ metric and the adjusted IQ reference are being used.

FIG. 1 illustrates one example of a computed tomography (CT) imaging system 100. The CT imaging system 100 is configured to image a subject 112 such as a person, an inanimate object, one or more manufactured parts, and/or foreign objects such as dental implants or stents. For simplicity, the subject 112 is referred to as a "person" or "patient" in the present application. It should be understood, however, that the subject matter described herein may also be applicable to other subjects, such as inanimate objects.

In one embodiment, the CT imaging system 100 includes a gantry 102 and at least one x-ray source 104 that is configured to project a beam of x-ray radiation 106 (hereinafter referred to as an "x-ray beam") for use in imaging the person. The x-ray beam 106 may also be referred to as x-rays or x-ray radiation. More specifically, the x-ray source 104 is configured to operate at a tube current and at a tube potential while generating the x-ray beam 106. The x-ray source 104 projects the x-ray beam 106 towards a CT detector 108 that is positioned on the opposite side of the gantry 102. The CT detector 108 is configured to collect projection data of a person. The x-ray source 104 is supplied power through a generator (not shown), such as the generator 215 (shown in FIG. 2). In some embodiments, at least a portion of the generator (e.g., a second stage) rotates with the x-ray source 104.

Although FIG. 1 depicts only a single x-ray source 104, in certain embodiments, multiple x-ray sources may be employed to project a plurality of x-ray beams 106 for acquiring projection data corresponding to the person at different energy levels to increase the scanned volume size, or to scan a volume more quickly.

During operation of the x-ray source 104 in some embodiments, a filament (e.g., tungsten filament) is heated by passing an electrical current therethrough. The heating enables electrons to be released from the filament through thermionic emission. The electrons are attracted toward a positively charged anode of the x-ray source 104 and collide with a designated target with a maximum energy that is determined by a tube potential (kV). One operating parameter of the x-ray source 104 is generally referred to as a tube current, which affects the energy and number of electrons released. As the electrons bombard the target x-ray photons are generated. The x-ray photons form the x-ray beam 106 with a range of energies (x-ray spectrum) that is directed out of a window of the x-ray source 104. Modifying the tube current can change the quantity of x-ray photons. Modifying the tube potential can change the quantity of x-ray photons, an average energy of the beam, and a maximum energy of the beam.

In certain embodiments, the CT system 100 further includes at least one processing unit 110 that may receive operator inputs, control operation of the x-ray source 104 and the generator 215, and at least partially process projection data. For example, the at least one processing unit 110 may be configured to reconstruct images of a region of interest (ROI) of the person using an iterative or analytic image reconstruction technique. The at least one processing unit 110 may be part of a computing system that is configured to execute programmed instructions stored in memory. The at least one processing unit 110, when executing the programmed instructions, may be configured to execute steps set forth herein. For example, the at least one processing unit 110 may use an analytic image reconstruction approach, such as FBP or IR, to reconstruct images of the ROI of the person.

In particular embodiments, the IR may be advanced statistical iterative reconstruction (ASIR). As other examples, the at least one processing unit 110 may use conjugate gradient (CG), maximum likelihood expectation maximization (MLEM), model-based iterative reconstruction (MBIR), and so on to reconstruct images of a ROI of the person.

Figure 2:
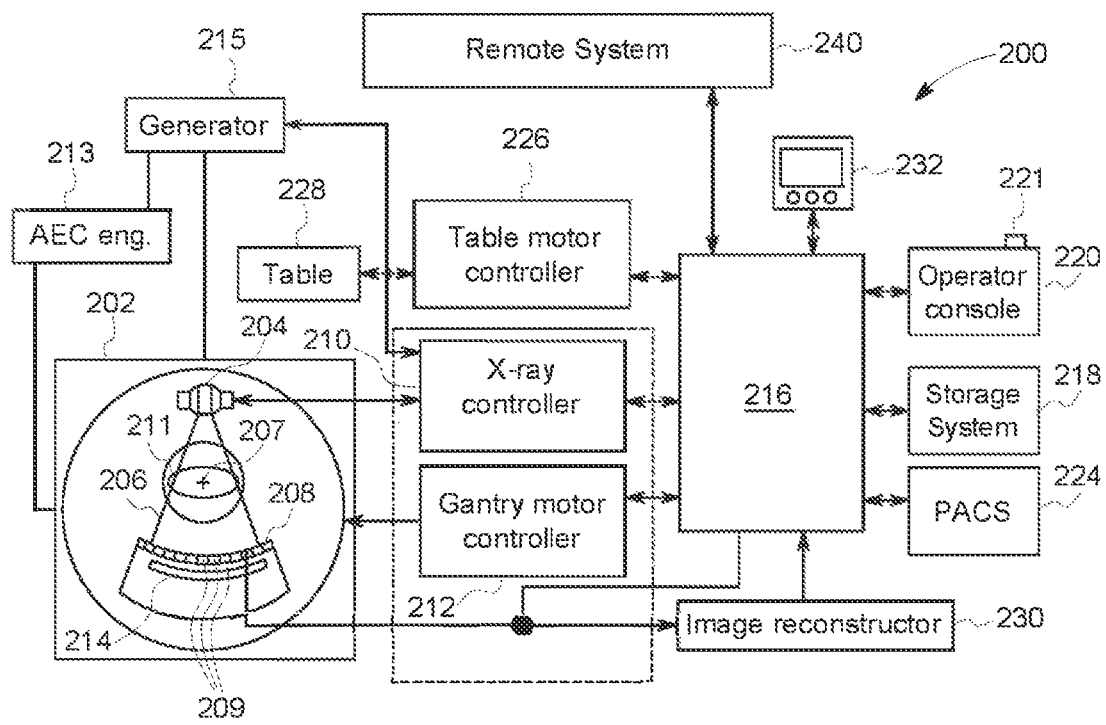
FIG. 2 illustrates a schematic diagram of a CT imaging system in accordance with an embodiment.

FIG. 2 illustrates a schematic diagram of a system 200. The system 200 may be a CT imaging system or may include one or more CT imaging systems. For example, the system 200 may include a remote system 240 that communicates with the CT imaging systems. The system 200 is hereinafter referred to as the CT imaging system 200. The CT imaging system 200 may be similar or identical to the CT imaging system 100 (FIG. 1). For example, the CT imaging system 200 includes a gantry 202, an x-ray source 204, a generator 215, a CT detector 208, and at least one processing unit 216. The at least one processing unit 216 may also be referred to as a computing system or processing system. The CT detector 208 includes a plurality of detector elements 209 that collectively detect the x-ray beam 206 that passes through and is attenuated by a person 211 (such as a person-under-examination) to acquire corresponding projection data. Accordingly, in some embodiments, the CT detector 208 is fabricated in a multi-slice configuration including the plurality of rows of cells or detector elements 209. In such a configuration, one or more additional rows of the detector elements 209 are arranged in a parallel configuration for acquiring the projection data.

The generator 215 provides a tube potential (or voltage) for the x-ray source 204. Optionally, the generator 215 may also provide timing signals to the x-ray source 204. The generator 215 may output different voltage levels to the x-ray source 204 during a CT scan. In some embodiments, a first voltage and a second voltage may be outputted in a fast-switching pattern such that the voltage increases and decreases in a sinusoidal manner between a maximum first voltage and a minimum second voltage (e.g., 140 kVp and 80 kVp). Optionally, the generator 215 may cause the first voltage and the second voltage to be effectively switched at a frequency of up to 550 Hz, up to 2 kHz, or more. By rapidly switching the voltage supplied to the x-ray source 104, samples may be obtained at low energy levels (80 kVp) and high energy levels (140 kVp).

However, the generator 215 may output different voltages in a pattern that is not fast-switching. For example, the generator 215 may switch from a first output voltage to a second output voltage only once during the CT scan. As another example, the generator 215 may power the x-ray source 204 at a first voltage level during a first CT scan of the person 211 and then power the x-ray source 204 at a second voltage level during a second CT scan of the same person 211 that immediately follows the first CT scan.

In certain embodiments, the CT imaging system 200 is configured to traverse different angular positions around the person 211 for acquiring desired projection data. Accordingly, the gantry 202 and the components mounted thereon may be configured to rotate as a unit about a center of rotation 207 for acquiring the projection data. For example, the generator 215, the x-ray source 204, and the CT detector 208 may be secured in fixed positions with respect to the gantry 202 when rotated circumferentially about the center of rotation 207 as a group.

The CT imaging system 200 also includes an x-ray controller 210 configured to provide power and timing signals to the x-ray source 204 and the generator 215. The x-ray controller 210 may include a dedicated processor and/or hardwired circuitry and may form a portion of the at least one processing unit. The x-ray controller 210 may receive commands from an AEC engine 213. Additionally, the CT imaging system 200 includes a gantry motor controller 212 configured to control a rotational speed and/or position of the gantry 202 based on imaging requirements.

The CT imaging system 200 may also include a data acquisition system (DAS) 214 that is configured to sample analog data received from the detector elements 209 and convert the analog data to digital signals for subsequent processing. The data sampled and digitized by the DAS 214 is transmitted to the at least one processing unit 216. In one example, the at least one processing unit 216 stores the data in a storage system 218. The storage system 218, for example, may include memory, hard disk drive, a solid-state storage device, a floppy disk drive, a compact disk-read/write (CD-R/W) drive, a Digital Versatile Disc (DVD) drive, and/or a flash drive.

The at least one processing unit 216 may include one or more processing units (e.g., a combination of processors, hardwired circuitry, or other logic-based devices) distributed throughout the CT imaging system 200. The at least one processing unit 216 is configured to execute programmed instructions stored in the storage system 218. While executing the programmed instructions, the at least one processing unit 216 is configured to control operation of the x-ray source 204 and the generator 215, among other things.

As used herein, the phrase "at least one processing unit" includes the possibility of multiple processing units (e.g., processors, hardwired circuitry, or other logic-based devices) distributed to different parts of the CT imaging system 200 or located at one confined area. For example, the phrase "at least one processing unit" may include a combination of one or more processing units of the x-ray controller 210, one or more processing units of the gantry-motor controller 212, one or more processing units of a table-motor controller 226, and one or more processing units of the image reconstructor 230. Optionally, the at least one processing unit 216 may include one or more processing units that are located remotely and/or shared with other CT imaging systems. For example, the remote system 240 may include the image reconstructor 230. The at least one processing unit 216 may execute programmed instructions stored in memory to direct components of the CT imaging system 200 to operate as described herein. Optionally, the at least one processing unit 216 may include one or more processing units that are shared with other CT imaging systems and/or located remotely.

Additionally, the at least one processing unit 216 provides commands and parameters to one or more of the DAS 214, the x-ray controller 210, and the gantry motor controller 212 for controlling system operations such as data acquisition and/or processing. In certain embodiments, the at least one processing unit 216 controls system operations based on operator input. The at least one processing unit 216 receives the operator input, for example, including commands and/or scanning parameters via an operator console 220 operatively coupled to the at least one processing unit 216. The operator console 220 may include an input device 221, such as a keyboard, touchpad, mouse and the like. The operator console 220 may also include a display 232. Optionally, the input device 221 includes the display 232, which may be a touch-sensitive screen. The input device 221 may enable the operator to input, for example, reference protocols, the IQ references (e.g., noise index, reference image, standard deviation, task-based IQ metrics) and/or system features (e.g., scan parameters).

Although FIG. 2 illustrates only one operator console 220, more than one operator console may be coupled to the CT imaging system 200, for example, for inputting or outputting system features, requesting examinations, and/or viewing images. Further, in certain embodiments, the CT imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In some embodiments, the CT imaging system 200 is controlled, at least in part, by the remote system 240. The CT imaging system 200 and the remote system 240 may have a client-server relationship in which the CT imaging system 200 communicates information and requests to the remote system 240 and receive responses to the requests. The requests may include, for example, a request for an adjusted IQ reference or an exposure-control parameter based on operator inputs that are communicated by the at least one processing unit 216. In such instances, one or more processing units of the at least one processing unit 216 may form part of the remote system 240.

In one embodiment, for example, the CT imaging system 200 either includes, or is coupled to a picture archiving and communications system (PACS) 224. In one example implementation, the PACS 224 is further coupled to the remote system 240. The remote system 240 may be or form part of, for example, a radiology department computing system, or a hospital computing system. The remote system 240 may form part of an internal or external server network (e.g., cloud-computing network). The remote system 240 may allow operators at different locations to supply operator inputs and receive answers to requests or other information.

In particular embodiments, the remote system 240 enables users to retrieve, update, and store designated protocols and/or other information. For example, the remote system 240 may include a database of reference protocols. After receiving information from the operator, the remote system 240 may suggest a reference protocol or a scan prescription for the clinical task. The remote system 240 may also have the databases described herein for retrieving weighting factors.

The at least one processing unit 216 uses the operator-supplied and/or system-defined commands and parameters to operate a table motor controller 226, which in turn, may control a motorized table 228. Particularly, the table motor controller 226 moves the motorized table 228 to appropriately position the person 211 in the gantry 202 for acquiring projection data corresponding to the ROI of the person 211.

As previously noted, the DAS 214 samples and digitizes the projection data acquired by the detector elements 209. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the at least one processing unit 216. Alternatively, the image reconstructor 230 may be absent from the CT imaging system 200 and instead the at least one processing unit 216 may perform one or more functions of the image reconstructor 230. Moreover, the image reconstructor 230 may be located locally or remotely, and may be operatively connected to the CT imaging system 200 using a wired or wireless network. Particularly, one exemplary embodiment may use computing resources in a cloud-computing network for the image reconstructor 230.

In one embodiment, the image reconstructor 230 reconstructs the images stored in the storage system 218. Alternatively, the image reconstructor 230 transmits the reconstructed images to the at least one processing unit 216 for generating useful information for diagnosis and evaluation. In certain embodiments, the at least one processing unit 216 transmits the reconstructed images and/or the information to the display 232.

The various methods and processes described further herein may be stored as executable instructions in non-transitory memory in the CT imaging system 200. The memory may form a portion or all of the storage system 218. In some embodiments, the image reconstructor 230 may include such instructions in non-transitory memory, and may apply the methods described herein to reconstruct an image from projection data. In another embodiment, the at least one processing unit 216 may execute the instructions from non-transitory memory, and may apply the methods described herein, at least in part, to a reconstructed image after receiving the reconstructed image from image reconstructor 230. In yet another embodiment, the methods and processes described herein may be distributed across image reconstructor 230 and the at least one processing unit 216.

In some embodiments, the display 232 allows the operator to evaluate the imaged anatomy. The display 232 may also allow the operator to select a volume of interest (VOI) and/or request person information, for example, via graphical user interface (GUI) for a subsequent scan or processing.

The following describes calculating a task-based IQ metric and using the task-based IQ metric to determine (e.g., calculate) other parameters, such as an adjusted IQ reference or an exposure-control parameter. Although the following describes calculating the task-based IQ metric with respect to reconstruction algorithms, it should be understood that the task-based IQ metric may be used with respect to other scan parameters. The scan parameter may have a relationship to radiation dose that is caused by the CT scan and/or may have a relationship to an image quality of the resulting image data. For example, the scan parameter that may differ between two reference protocols may be a tube potential, a gantry rotation time or speed, an operating configuration for the CT detector, a slice thickness, or a helical pitch.

In some embodiments, the task-based IQ metric may be used to adjust inputs for the CT imaging system so that the radiation dose and/or the image quality from the different protocols are essentially equal. The different protocols may be performed by the same CT imaging system. In some embodiments, however, the different protocols are performed by different CT imaging systems. For example, the different CT imaging systems may be the same type of CT imaging system (e.g., identical equipment and software). The different CT imaging systems may be different versions within a product family that is produced by the same vendor. The different CT imaging systems may be different types from the same vendor, or the different CT imaging systems may be different types from different vendors.

The other system features of the different protocols may be identical or nearly identical. For example, each and every other system feature of each protocol may be the same, except for the modified system feature (e.g., reconstruction algorithm). However, in other embodiments, more than one system feature may differ between the two protocols.

The task-based IQ metric may be determined using a detectability index. The detectability index is a task-based, frequency-dependent signal-to-noise ratio (SNR) metric that combines the spatial resolution (MTF) and noise properties (NPS) of an imaging system and the spatial-frequency content of a task object. In particular embodiments, the task-based IQ metric is derived from a non-prewhitening detectability index. The non-prewhitening detectability index can be defined as:

$$d'^2 = \frac{\left(\iint W_{task}^2(u,v) MTF_{task}^2(u,v) du\, dv\right)^2}{\iint W_{task}^2(u,v) MTF_{task}^2(u,v) NPS(u,v) du\, dv} \quad (1)$$

where $MTF_{task}$, is the task-based modular transfer function (MTF), NPS is the noise power spectrum, and $W_{task}$ represents the frequency content of the signal. $MTF_{task}$ characterizes how a CT imaging system responds to different spatial frequencies for a designated clinical task. $MTF_{task}$ may also be characterized as the capacity of a CT detector to transfer modulation of an input signal at a given spatial frequency to its output for a designated clinical task. NPS is a function of the magnitude and the texture of noise. $W_{task}$ may indicate the spatial frequencies that are relevant for a designated clinical task.

Optionally, $W_{task}$ may be calculated analytically using the following expression for a 2D Gaussian, with full width at half maximum (FWHM) equal to the task diameter and where C is the contrast of the task with respect to the background:

$$W_{task} = C \, \exp\!\left(-\frac{x^2+y^2}{FWHM^2}\ln(2)\right) \quad (2)$$

For certain nonlinear iterative reconstruction algorithms, the system noise and resolution properties may vary with noise magnitude and object contrast. To incorporate the effect of contrast-dependent resolution, $MTF_{task}$ can be estimated from contrast elements in a phantom by estimating the edge spread function.

If the NPS is normalized by its integral across frequencies, the NPS can be written as a product of the normalized nNPS and noise variance, thereby separating noise magnitude from noise texture. With this substitution, the expression for $d'^2$ in equation (1) can be rewritten as:

$$d'^2 = \frac{\left(\iint W_{task}^2(u,v) MTF_{task}^2(u,v) du\, dv\right)^2}{\sigma^2 \iint W_{task}^2(u,v) MTF_{task}^2(u,v) nNPS(u,v) du\, dv} \quad (3)$$

where σ is an IQ reference (e.g., noise index). W task is independent of radiation dose, but changes with the shape and contrast of the object of interest. $MTF_{task}$ and nNPS are generally independent of dose for linear reconstruction algorithms, except for very low dose with electronic noise correction may be employed.

Equation (3) may be inverted to calculate the σ needed to obtain the prescribed $d'^2$:

$$\sigma^2 = \frac{\left(\iint W_{task}^2(u,v) MTF_{task}^2(u,v) nNPS(u,v) du\, dv\right)2}{d'^2 \iint W_{task}^2(u,v) MTF_{task}^2(u,v) nNPS(u,v) du\, dv} \quad (4)$$

For iterative reconstruction algorithms, the amount of blurring may vary with the dose/noise level. Optionally, $MTF_{task}$ and nNPS may be assumed as being constant with dose. Accordingly, the equation (3) can also be rewritten as:

$$d'_{gen} = \frac{K}{\sigma} \quad (5)$$

where $d'_{gen}$ is a generalized metric (also referred to herein as "task-based IQ metric") that represents overall image quality, K depends on the reconstruction method and the task object that is selected to represent image quality for a scan, and σ represents a noise parameter (e.g., noise standard deviation) that may be provided by an operator. Optionally, K may depend on other parameters, such as a tube potential, a gantry rotation time or speed, an operating configuration for the CT detector, a slice thickness, or a helical pitch.

From equation (5), the noise standard deviation (or noise index) may be converted to $d'_{gen}$ for a designated scan prescription that differs from a reference scan prescription. Equation (5) can enable identifying an adjusted noise standard deviation that is needed to produce a specific $d'_{gen}$ value for the designated scan prescription. AEC methods may then use the adjusted noise standard deviation to select the TCM profile to provide the adjusted noise standard deviation.

AEC methods may set the noise standard deviation equal to a in the above equation. The adjusted noise standard deviation is task-based, because the adjusted noise standard deviation implicitly accounts for contrast, spatial resolution, and noise texture.

To generate databases for $d'_{gen}$ estimation, the American College of Radiology (ACR) 20-cm-diameter phantom was scanned on a Revolution CT (GE Healthcare) at 120 kV and with tube current varied between 25 and 200 mAs. Images were reconstructed with 2.5 mm slice thickness using a reference FBP-type reconstruction algorithm and varying levels of an in-house iterative reconstruction algorithm (IR1, IR2, IR3 and IR4), which may be similar to the adaptive statistical iterative reconstruction (ASIR) developed for the Revolution CT (called ASIR-V). The acrylic rod object within the ACR phantom was chosen to represent the task for the evaluated implementation of the method. The task-based MTF, $MTF_{task}$, was calculated from regions of interest extracted around the acrylic objects.

NPS was calculated from the uniform section of module 3 of ACR phantom. A total of 200 ROIs of 128×128 pixels from 80 axial image slices were used to calculate the NPS. Databases (e.g., lookup tables) were generated to store the $MTF_{task}$, nNPS, and $W_{task}$ for the different reconstruction algorithms, which can be used to calculate the K factors (Eq. (4)) for converting between noise standard deviation and $d_{gen}'$.

Accordingly, the AEC engine may control the x-ray source according to a TCM profile that is based on the adjusted noise standard deviation to produce image data having an image quality that essentially matches the image quality expected by the operator when using the target IQ reference. As a particular example, the AEC engine may control the x-ray source according to a TCM profile that is based on the adjusted noise standard deviation for a reference protocol that uses an iterative reconstruction algorithm. The resulting image data may have an image quality that essentially matches the image quality expected by the operator when using the noise index and FBP reconstruction.

Embodiments set forth herein may generate or use databases (e.g., lookup tables (LUTs)) of weighting factors for calculating the task-based metric ($d'_{gen}$) or the noise standard deviation. The weighting factors include $MTF_{task}$, $W_{task}$ and nNPS and the K factor, which may be a constant value that is a function of $MTF_{task}$, $W_{task}$, and nNPS. The weighting factors may be used to convert a noise standard deviation to a $d'_{gen}$ or to covert a $d'_{gen}$ to a noise standard deviation.

The values for $MTF_{task}$ can be determined by at least one of experiments, simulations, or one or more analytical models. $MTF_{task}$ values may change with the reconstruction algorithm and with a task object contrast level. $W_{task}$ values can be obtained by one or more analytical models. nNPS values can be determined by at least one of experiments, simulations, or one or more analytical models. The different values may be collected in respective databases that are also identified by qualities of the task object and one or more parameters that affect radiation dose or image quality, such as the reconstruction algorithm or tube potential. As described above, constant values for the K factor may be calculated and assigned to databases that are also identified by qualities of the task object and one or more parameters that affect radiation dose or image quality. More specifically, each database may be identified by a combination of one or more task object qualities (e.g., size, shape, contrast) and one or more parameters that affect radiation dose or image quality.

To illustrate, a first database may assign a K factor value of 2500 for image data reconstructed with FBP and having a task object that is 5 mm in size, circular in shape, having a high contrast. A second database may assign a K factor value of 1800 for image data reconstructed with an iterative reconstruction (10% level) and having a task object that is 5 mm in size, circular in shape, having a high contrast. A third database may assign a K factor value of 1700 for image data reconstructed with an iterative reconstruction (20% level) and having a task object that is 5 mm in size, circular in shape, having a high contrast. A fourth database may assign a K factor value of 1500 for image data reconstructed with an iterative reconstruction (30% level) and having a task object that is 5 mm in size, circular in shape, having a high contrast.

Accordingly, databases (e.g., LUTs) may be used to determine a K factor constant value that can be used to convert an IQ reference (e.g., noise index) to a task-based IQ metric ($d'_{gen}$) and vice-versa.

In some embodiments, databases may be used to determine each one of (or a combination of) the weighting factors, such as $MTF_{task}$, $W_{task}$, and nNPS instead of the K factor. For example, a database for $MTF_{task}$ can be made, a database for $W_{task}$ can be made, and a database for nNPS can be made. Optionally, a database for the product of two factors (e.g., $MTF_{task}$ and $W_{task}$) can be made. Values from the databases may be retrieved and used as weighting factors to calculate the task-based IQ metric or the noise standard deviation.

As described above, each database may have a K factor constant value indexed to a different combination of task object qualities and one or more other parameters (e.g., reconstruction algorithm). To retrieve the K factor, the at least one processing unit may identify the database having the K factor using information (e.g., clinical task and reconstruction algorithm) provided by the operator or the system. Several databases may be made for parameters of interest (e.g., reconstruction algorithm, tube potential, etc.).

With the databases constructed, an operator may be able to obtain a desired image quality using a modified parameter in which the desired image quality is similar to the image quality of image data obtained using a different parameter. With the K factor databases constructed, an adjusted noise standard deviation GB may be determined using the following formula:

$$\sigma_B = \sigma_A \frac{K_{task\_paramB}}{K_{task\_paramA}}$$

where $K_{task\_paramA}$ represents the K factor constant for the reference parameter (e.g., known reconstruction algorithm), $K_{task\_paramB}$ represents the K factor constant for the modified parameter (e.g., prescribed reconstruction algorithm that is different from known reconstruction algorithm), GA represents the noise standard deviation that was selected by the operator that is associated with a desired image quality using the reference parameter, and GB represents the adjusted noise standard deviation that will be used by the AEC engine with the modified parameter. Accordingly, a ratio of simple constants and the noise standard deviation GA may be used to calculate the adjusted noise standard deviation GB for the modified parameter.

Figure 3:
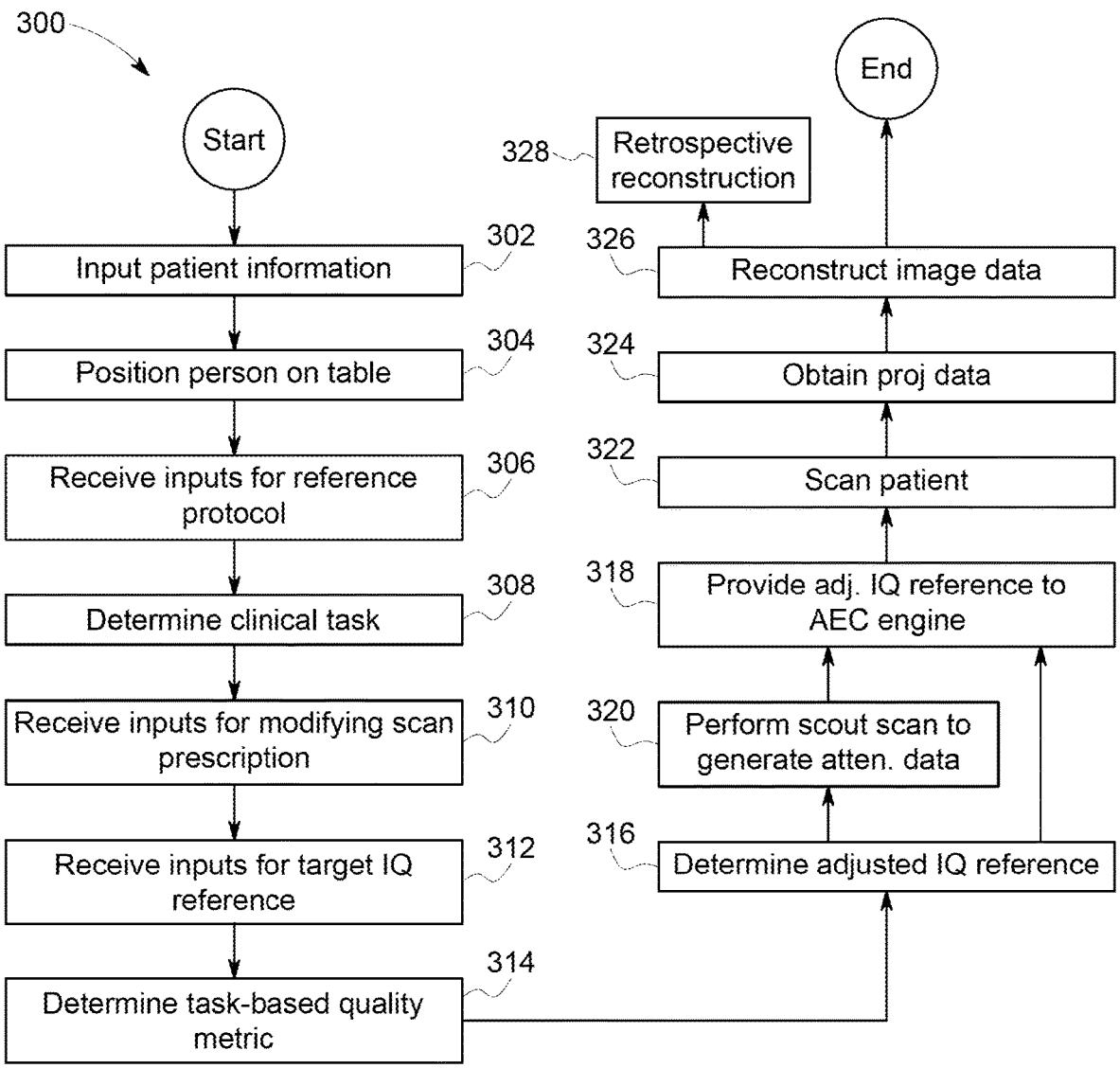
FIG. 3 is a flowchart illustrating a method of scanning a person in a CT imaging system in accordance with an embodiment.

FIG. 3 illustrates a method 300 in accordance with an embodiment. The method 300 may be, for example, a method of scanning a person in a CT imaging system. The method 300 employ structures or aspects of various embodiments (e.g., systems and/or methods) discussed herein. For example, at least some steps of the method 300 may be executed by at least one processing unit. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

The method 300 includes inputting, at 302, patient information into the CT imaging system. The patient information may include information that can affect attenuation. For example, the person information may relate to size and weight. At 304, the person may be positioned on a table that is configured to move into a gantry. Before or after positioning the person, the CT imaging system may receive, at 306, operator inputs for determining a reference protocol. The reference protocol prescribes system features that determine operation of the X-ray source and the CT detector during a CT scan. For example, the reference protocol may be determined, at 306, by receiving operator inputs that select a known protocol (e.g., from drop-down menu) or that create a new protocol. To create a new protocol, the operator may enter the appropriate information into a table.

A reference protocol includes a set of pre-programmed system features (e.g., settings and parameters of the CT imaging system) that determine operation of the CT imaging system. For example, the reference protocol may include a scan type (e.g., axial, helical); a scan field of view (SFOV) or region of interest (ROI) (e.g., head, chest, abdomen); a gantry rotation speed (e.g., one second for one rotation); a slice thickness; a beam collimation; a tube potential; one or more tube current parameters (e.g., tube current range or average tube current); a default IQ reference (e.g., noise index value); a reconstruction algorithm, including a reconstruction type and reconstruction kernel and (optionally) a level or strength; CT dose index ($CTDI_{vol}$), dose length product (DLP), scan length, and a phantom type used for dose calculation.

At 308, a clinical task is determined. In some embodiments, the system may automatically determine the clinical task based on the reference protocol and/or other information, such as the personal information. In some cases, a reference protocol may be associated with only one clinical task. As such, the clinical task may be determined, at 308, when the reference protocol is determined.

Alternatively, the clinical task, at 308, may be selected by the operator before selecting the reference protocol. For example, the operator may select a clinical task from a plurality of possible clinical tasks. The system may automatically determine the reference protocol, at 306, based on the clinical task selected by the operator.

When the operator selects the designated protocol and/or the clinical task, the at least one processing unit may populate the display with certain settings and parameters. The operator may be enabled to modify at least some of the settings and parameters of the designated protocol. For example, at 310, the CT imaging system may receive operator inputs for modifying one or more of the system features of the scan prescription. The operator may select a field on the display and enter an alphanumeric string (e.g., numerical value or name) or may select information from a menu. As an example, the operator may select a different reconstruction algorithm. A different reconstruction algorithm may be an algorithm that has same technique (e.g., iterative reconstruction) but may have a different levels or strengths (e.g., amount of iterative reconstruction). A different reconstruction algorithm may be another type of technique (e.g., FBP vs. IR). In some embodiments, the CT imaging system may automatically modify parameters in response to changes by the operator. For example, the CTDI may change based on changes made by the operator.

At 312, a target IQ reference is received by the CT imaging system through operator inputs. The target IQ reference represents an image quality desired by the operator. The target IQ reference may be a reference value associated with a known standardized table (e.g., commercially-developed standard for designated CT imaging systems). The operator may be familiar with the known standard through experience in using the CT imaging system or other CT imaging systems that use the same standard. The image quality associated with the target IQ reference represents an image quality for images acquired with reference system features (e.g., predetermined settings and parameters).

For example, the operator may enter the a noise index that effectively requests the image data to have approximately equal image noise. As another example, the operator may enter the a reference mAs that effectively requests the image data to have an approximately equal effective tube current-time product. The effective tube current-time product may be defined as the product of tube current and rotation time divided by pitch in a helical scan mode.

In each of the above examples, the operator may be selecting a value based on past experience with the CT imaging system for the clinical task. As noted above, however, the operator may change settings or parameters that deviate from the default settings or parameters of the reference protocol/clinical task. For example, the operator may have selected, at 310, an iterative reconstruction algorithm for a reference protocol/clinical task that previously used FBP for processing the image data. Thus, the target IQ reference may represent an image quality obtained using FBP that the operator would like to have for the new reconstruction algorithm. But, as described above, such user-selected IQ references may not be equally applicable for different reconstruction algorithms.

At 314, a task-based IQ metric may be determined using the target IQ reference and the prior reconstruction algorithm and/or scan parameter. The task-based IQ metric may then be used to determine an adjusted IQ reference, at 316, that will be used by the CT imaging system.

Figure 4:
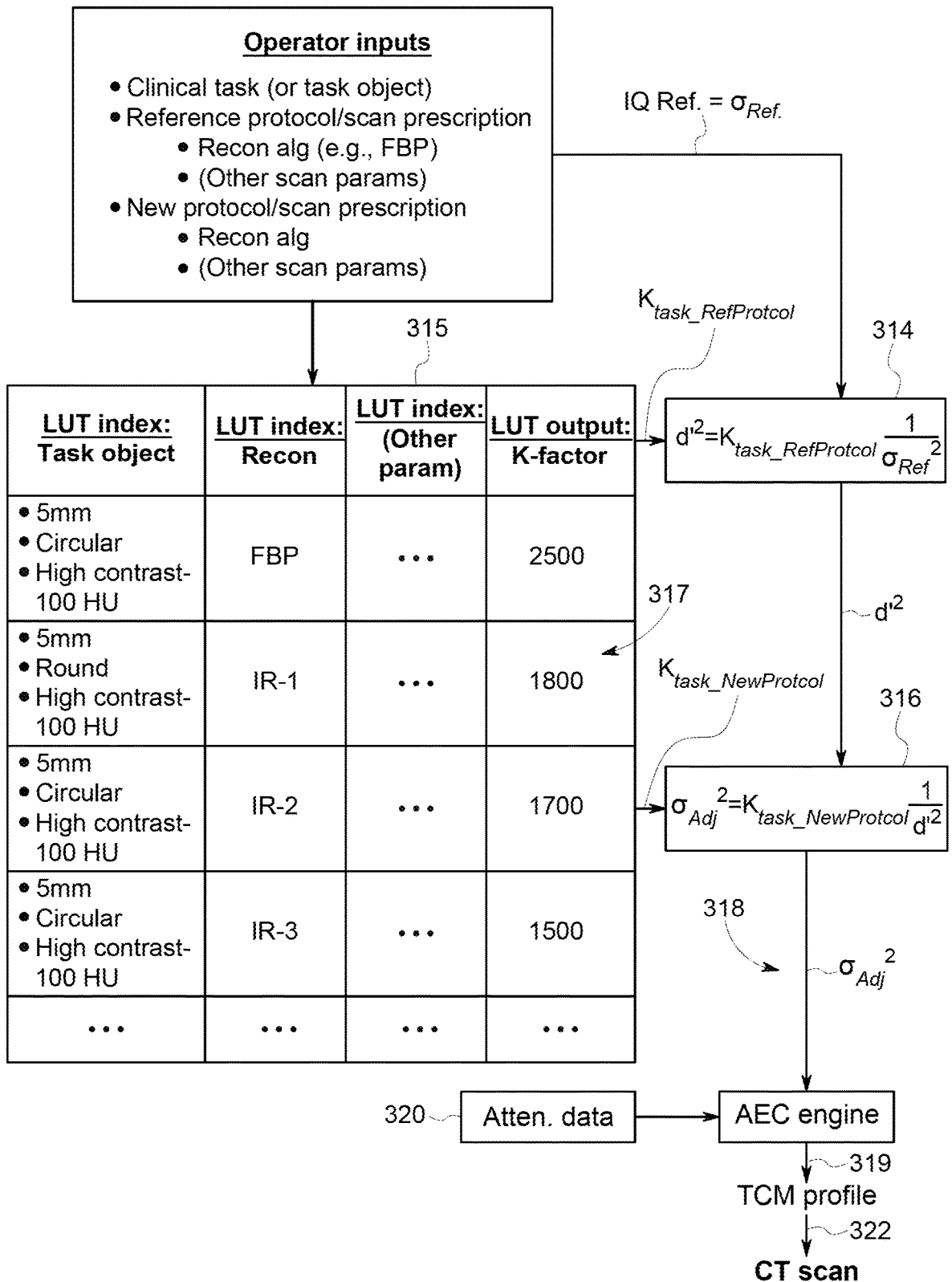
FIG. 4 illustrates a method of adjusting an image quality (IQ) reference input by the operator based on a task object and a modified system feature.

FIG. 4 illustrates how the task-based IQ metric and the adjusted IQ reference may be determined, at 314 and 316 (FIG. 3), respectively, in greater detail. Databases (or tables) may exist for different combinations of variables. The variables may include, for example, the size of the task object, the shape of the task object, the contrast of the task object, and one or more other features, such as a reconstruction algorithm or a scan parameter that affects radiation dose and/or image quality.

In some embodiments, each database corresponds to a unique combination of the variables. The databases may include weighting factors (e.g., constant values) that are indexed to be used in subsequent calculations. To retrieve the weighting factor, the at least one processing unit may identify the database that has each of the parameters for the scan prescription. As shown in FIG. 4, a database array 315 includes a plurality of databases (e.g., tables or rows) 317. Each of the databases 317 includes a task object for a designated clinical task, which is identified by the different task object qualities. Each of the databases 317 includes a reconstruction algorithm (e.g., FBP). Similar to the task objects, the reconstruction algorithms may have a plurality of qualities or features.

The database array 315 may be searched or interrogated to identify whether any K factors exists that match the operator inputs for the reference scan prescription. For example, the at least one processing unit may communicate the clinical task or qualities of the associated task object and the reconstruction algorithm. Alternatively or in addition to the reconstruction algorithm, a scan parameter that affects radiation dose and/or image quality may be provided. The database array 315 may identify the appropriate K factor and output the $K_{task\_RefProtocol}$ factor. Optionally, embodiments may estimate the K factor if a K factor cannot be identified using the operator inputs.

In a similar manner, the database array 315 may be searched or interrogated to identify whether any K factors exists that match the operator inputs for the new scan prescription. For example, the at least one processing unit may communicate the clinical task or qualities of the associated task object and the reconstruction algorithm. Alternatively or in addition to the reconstruction algorithm, a scan parameter that affects radiation dose and/or image quality may be provided. The database array 315 may identify the appropriate K factor and output the $K_{task\_NewProtocol}$ factor. Optionally, embodiments may estimate the K factor if a K factor cannot be identified using the operator inputs.

Also shown, the target IQ reference (IQ Ref) provided by the operator inputs may be converted to a noise standard deviation $\sigma_{Ref}$. For example, if the target IQ reference is a noise index, then the target IQ reference may be transmitted without further modification. If the target IQ reference is a reference image or a reference mAs, the target IQ reference may be processed to provide a noise standard deviation $\sigma_{Ref}$. For example, the reference image may be examined to determine the noise standard deviation. The reference mAs may be converted using a known conversation index or model.

At a first operation 314, a $d'^2$ (or a task-based IQ metric) may be calculated using the $\sigma_{Ref}$ and the $K_{task\_RefProtocol}$. The $d'^2$ represents the overall image quality of the reference image data. The $d'^2$ may then be supplied to operation 316 for calculating the adjusted IQ reference ($\sigma_{Adj}$) or ($\sigma_{Adj}^2$) using the $K_{task\_NewProtocol}$. The adjusted IQ reference ($\sigma_{Adj}$) or ($\sigma_{Adj}^2$) may then be communicated to the AEC engine at 318. The AEC engine uses the adjusted IQ reference for determining a TCM profile at 319. Optionally, the AEC engine may use data from a scout scan that was performed at 320 and provide the attenuation data to the AEC engine.

Alternatively, the database array 315 may include other information. For example, respective databases may exist for determining the weighting factors MTFtask, nNPS, and Wtask associated with the task object qualities and FBP, and respective databases may exist for determining the weighting factors MTFtask, nNPS, and Wtask associated with the task object qualities and IR.

Returning to FIG. 3, at 322, the person may be scanned and projection data may be obtained, at 324. The projection data, at 326, may be processed to form medical images. Optionally, a retrospective reconstruction may be performed, at 328. For example, a different target IQ reference may be selected, at 312, and/or a new reconstruction algorithm, at 310.

In some embodiments, at least some of the operations for the method 300 may be performed offline and/or by a remote system, such as the remote system 240. For example, a healthcare provider may have a gantry, x-ray source, generator, table, a console for receiving inputs, and a local computing system. The local computing system may include one or more controllers for operating the gantry, x-ray source, generator, and table. The operator may enter inputs into the console. The local computing system may communicate data to the remote system.

Figure 5:
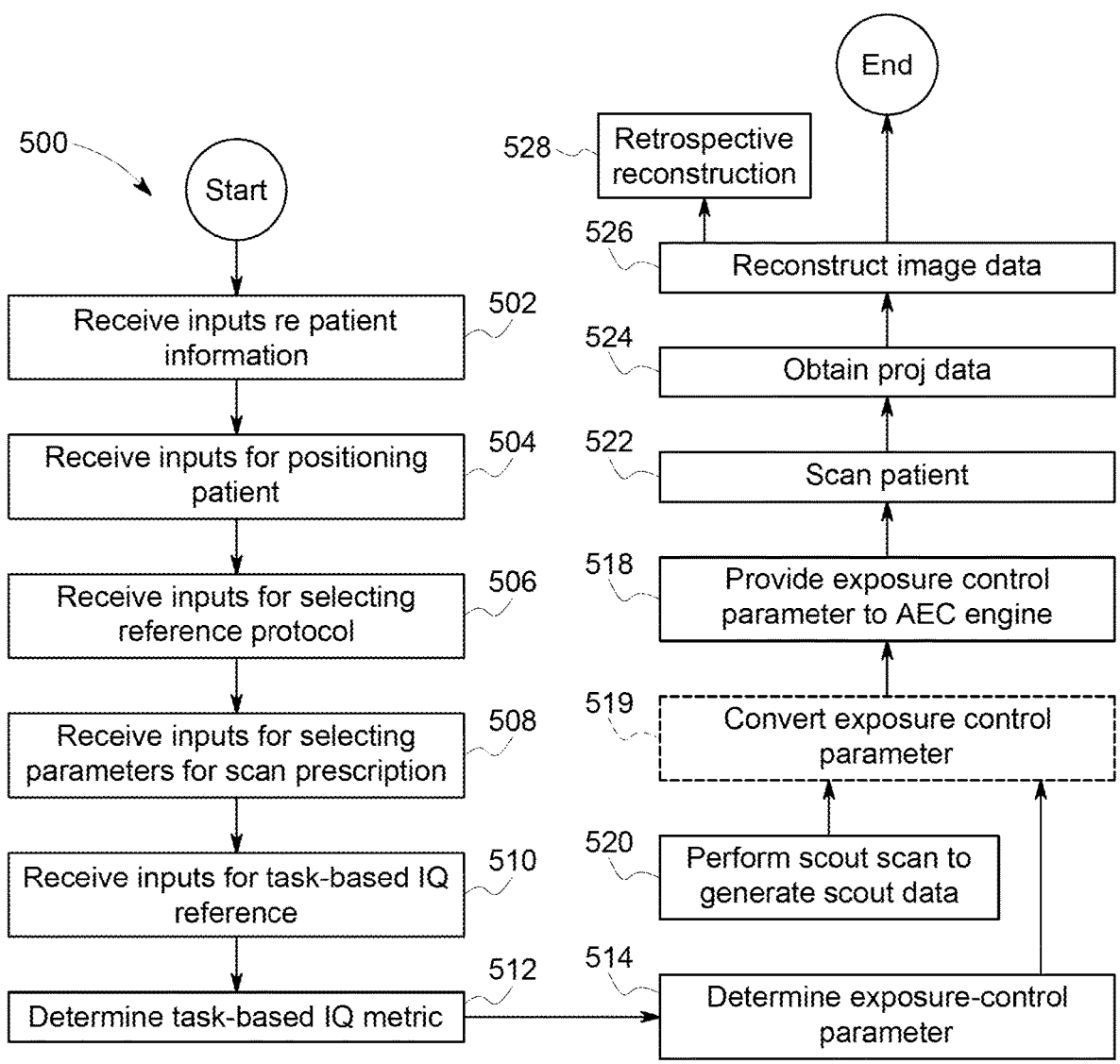
FIG. 5 is a flowchart illustrating a method of scanning a person in a CT imaging system in accordance with an embodiment.

FIG. 5 is a flowchart illustrating a method 500 that may be, for example, a method of scanning a person in a CT imaging system. The method 500 employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

The method 500 may include steps that are similar or identical to the steps of the method 300 (FIG. 4). At 502, patient information may be input into the CT system and the person may be positioned at 504. At 506, operator inputs for selecting a reconstruction algorithm and a clinical task having a task object may be received. Optionally, the operator inputs may include selecting a reference protocol having the clinical task and, optionally, the reconstruction algorithm. After selecting the reference protocol the operator may modify any system features associated with the reference protocol. For example, the display may populate a table with suggested scan parameters and values or selections for those scan parameters. At 508, the operator may select or confirm parameters for a scan prescription.

Figure 6:
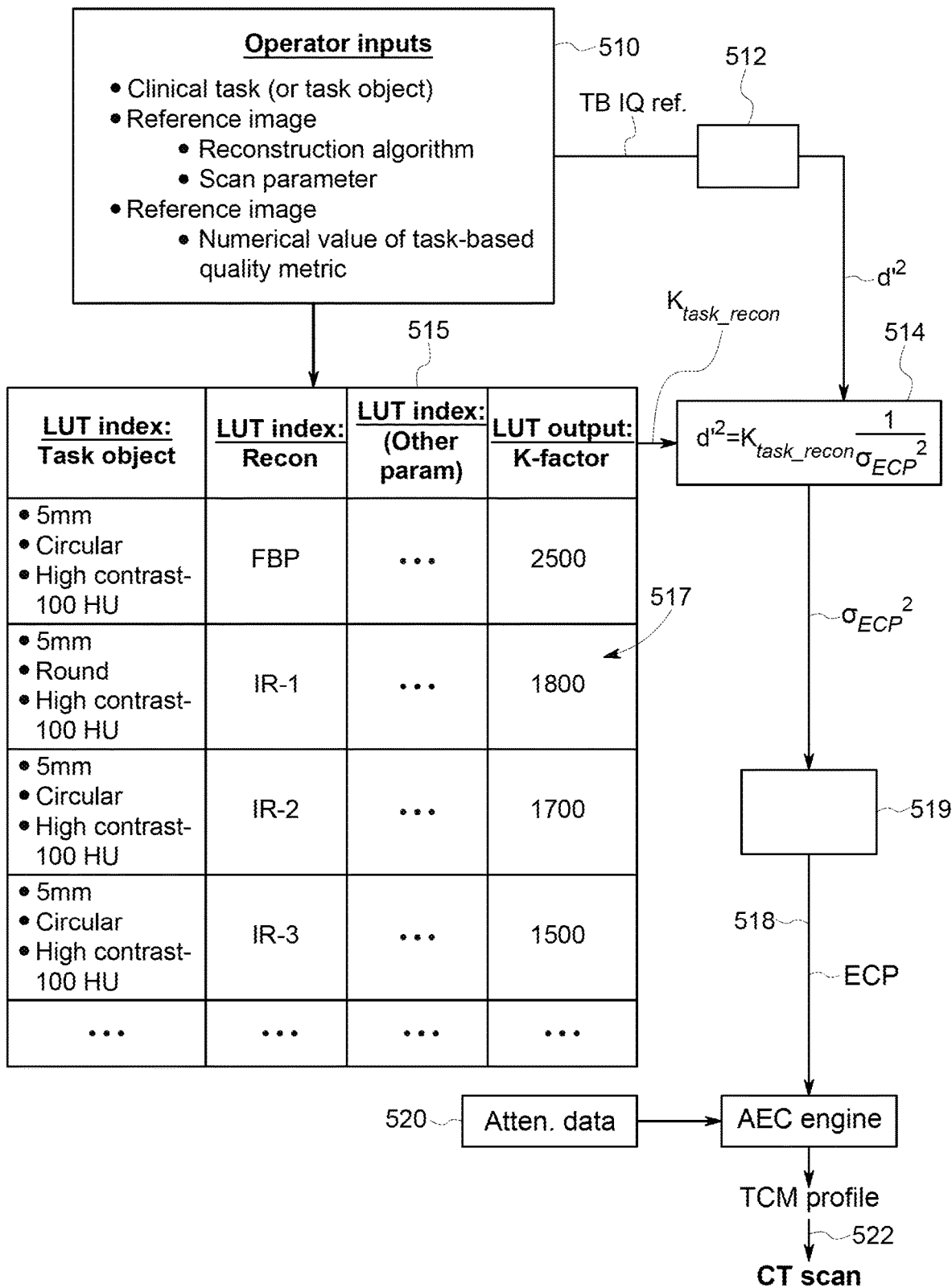
FIG. 6 illustrates a method of generating an exposure-control parameter based on operator inputs.

FIG. 6 illustrates a method for determining an exposure-control parameter in greater detail. FIGS. 5 and 6 are described together. At 510, operator inputs for determining a task-based IQ reference may be received. The task-based IQ reference represents a desired or acceptable image quality for the clinical task. In particular embodiments, the task-based IQ reference may be a reference image. For example, the operator may select a reference image having an overall image quality that the operator would like for the resulting image data. In some embodiments, the CT imaging display may present a set of reference images to the operator. The reference images of the set may be determined by the clinical task or the reference protocol. The operator may select, at 510, the reference image from the set.

At 512, a task-based IQ metric may be determined using the task-based IQ reference. For embodiments in which the task-based IQ reference is a reference image, the task-based IQ metric may be determined by at least one of using information stored with the reference image or analyzing the reference image. For example, the reference image may have a task-based IQ metric assigned to the reference image (e.g., stored in a database with the reference image). In other words, a $d'^2$ value may be assigned to the reference image. Alternatively, embodiments may analyze the reference image and calculate the task-based IQ metric. For example, at least one of a weighting factor or a noise standard deviation may be assigned to the reference image (e.g., stored in a database with the reference image). In other embodiments, a weighting factor may be retrieved from a database using known information (e.g., task object, reconstruction algorithm used to generate the reference image, etc.) and/or a noise standard deviation may be determined by analyzing the reference image (e.g., identifying one or more uniform regions in the reference image and calculating standard deviation therefrom).

The task-based IQ reference may also be a value that is directly entered by the operator. The value may be, for example, a numerical value or a relative value. A relative value may be provided by, for example, moving a virtual slider between top and bottom ends, wherein a higher image quality is desired if the slider is closer to the top end and a lower image quality is desired if the slider is closer to the bottom end.

A numerical value may be equal to the $d'^2$ value. For such embodiments, receiving operator inputs, at 510, and determining the task-based IQ metric, at 512, may occur at the same time. In other embodiments, however, the numerical value may be required to be within a standardized range of values. More specifically, $d'^2$ values may not have a readily identifiable meaning to the operator based on the $d'^2$ value alone. As such, a task-based range may be developed that is more meaningful to the operator. For example, values for the task-based range may be between 1-5 or 1-10. Multiple task-based ranges may exist and correlate to different tasks or combinations of variables (e.g., task object, reconstruction algorithm, scan parameter, etc.).

At 514 (FIG. 6), an exposure-control parameter $\sigma_{ECP}$ may be determined using the $d'^2$ value and a $K_{task\_recon}$ factor. As described above, the $d'^2$ value may be assigned to a reference image or may be calculated from the reference image as described herein. Alternatively, the $d'^2$ value may be directly entered by the operator. The $K_{task\_recon}$ factor may be obtained from a database array 515 using the operator inputs. For example, the $K_{task\_recon}$ factor may be retrieved from a database 517 using the qualities of the task object and the reconstruction algorithm for the resulting image data. Alternatively, the database array 515 may include other information. For example, respective databases may exist for determining the weighting factors MTFtask, nNPS, and Wtask associated with the task object qualities and the reconstruction algorithm. In other embodiments, the weighting factor(s) may be identified based on a selected scan parameter, such as kV, instead of a selected reconstruction algorithms.

In some embodiments, the exposure-control parameter $\sigma_{ECP}$ may be communicated directly to the AEC engine without further modification. In other embodiments, the exposure-control parameter $\sigma_{ECP}^2$ may be adjusted or converted, at 519, to an exposure-control parameter ECP. As described above, indexes or models may exist that convert the exposure-control parameter $\sigma_{ECP}$ to the exposure-control parameter ECP. The indexes or models may be based on, for example, a radiation dose or exposure. In some embodiments, the conversion indexes or models may be generated through experimentation, simulation, and/or modeling. For example, a noise index value may be converted to a reference mAs value.

At 518, the exposure-control parameter is provided to the AEC engine, which may generate a TCM profile. Optionally, at 520, a scout scan is performed to collect patient attenuation information. At 522, a CT scan may be performed in which the x-ray source is directed to generate the x-ray beam during the CT scan, wherein at least one of the tube current or the tube potential during the CT scan is a function of the exposure-control parameter. The CT scan may be based on a TCM profile. At 524, projection data is obtained and reconstructed to image data at 526. Optionally, the image data and/or the projection data may undergo retrospective reconstruction at 528.

In some embodiments, the systems and methods may be part of or used with a larger network of systems. For example, components of the CT imaging system 200 (FIG. 2) at a local site (e.g., healthcare provider) may be communicatively coupled to the remote system 240. The remote system 240 may be configured to control one or more operations performed by the CT imaging system 200. In some embodiments, the "at least one processing unit" includes one or more processing units located with the components (e.g., the gantry, x-ray source, CT detector, operator console, and a local computing system) at the local site and one or more processing units being located with the remote system 240.

For example, the operator may enter inputs for patient information, positioning a person on the table, selecting a reference protocol and/or a clinical task, selecting parameters for a scan prescription, and providing a task-based IQ reference as described above. For embodiments that utilize the remote system 240, the operator inputs are communicated to the remote system 240 and the operations or steps of receiving at 502, receiving at 506, receiving at 508, and receiving at 510 occur at the remote system 240. The inputs may be communicated directly to the remote system upon being entered by the operator or, optionally, the inputs may be packaged in a designated manner and communicated to the remote system 240 according to a predetermined protocol.

The remote system includes at least a portion of the at least one processing unit. The remote system may determine the task-based metric, at 512, and determine the exposure-control parameter, at 514. For example, the operator inputs may include a reference system feature, a modified system feature, a clinical task having a task object, and the task-based IQ reference. With the proper data, the remote system 240 may determine the exposure-control parameter, at 514, based on the task object, the modified system feature, and the task-based IQ metric. Optionally, the exposure-control parameter may be converted, at 519, to another exposure-control parameter that is suitable for subsequent calculations.

At 520, a scout scan may be performed by the healthcare provider to acquire scout data (e.g., patient attenuation data). If the TCM profile is determined at the remote system 240, the scout data may be communicated to the remote system 240. Optionally, the scout scan is performed at an earlier time and the scout data is communicated with earlier operator inputs, such as those from operations 502, 506, 508, and 510. At 518, the exposure-control parameter from 514 or, alternatively, from 519 and the optional scan data from 520 are provided to an AEC engine. The AEC engine may be part of the CT imaging system with the healthcare provider or may be part of the remote system 240. The AEC engine may determine a TCM profile using the exposure-control parameter and optional scan data.

If the TCM profile is generated by the remote system 240, the remote system 240 may communicate the TCM profile to the local components of the CT imaging system at the local site. The x-ray source may receive the TCM profile and be directed to generate the x-ray beam according to the TCM profile. Alternatively, the remote system may communicate the exposure-control parameter and the local portion of the CT imaging system may generate the TCM profile.

In some embodiments, the operator inputs that are selected involve different CT imaging systems. The methods 300 and 500 of FIGS. 3 and 5, respectively, may be carried in which the information used as a reference involves a different CT imaging system than the CT imaging system that will be used to acquire image data. More specifically, the operator may desire to obtain image data using a new CT imaging system. The operator may desire to acquire image data in which the image quality of the image data is essentially the same as the image quality for image data obtained using a different CT imaging system. For example, a reference system feature may be associated with image data that was acquired by a first CT imaging system. The modified system feature, which is selected or proposed by the operator, may be for acquiring image data using a second CT imaging system. The first and second CT imaging systems may be, for example, the same type or model (e.g., two General Electric (GE) Revolution HD scanners located in different hospitals). The different CT imaging systems may be different versions within a product family that is produced by the same vendor (e.g., a GE Revolution HD scanner and a GE Revolution CT scanner). The different CT imaging systems may be different types or models from the same vendor (e.g., a GE Discovery CT750 HD scanner and a GE Optima CT660 scanner), or the different CT imaging systems may be from different vendors (e.g., GE Discovery CT750 HD and a third-party CT scanner).

In such embodiments, the weighting factor(s) for different CT imaging systems may be developed independently due to, for example, different performances of the CT imaging systems. The different performances may be caused by different equipment (e.g., x-ray source, CT detector, filter) having different operating characteristics or by software that uses different algorithms (e.g., for generating a TCM profile). In other instances, the CT imaging systems are the same type or model having the same equipment, but the different performances are caused by differing amounts of usage, wear, and/or tolerances in manufacturing the respective CT imaging systems. Different imaging systems may have, for example, different modulation transfer functions (MTFs) and noise-power spectrums (NPSs).

The K factor associated with the reference system feature may be retrieved from a first database for the first CT imaging system. The K factor for the modified system feature may be retrieved from a second database for the second CT imaging system. A database of weighting factors may be generated through at least one of one or more experiments, one or more simulations, or one or more analytical models. For example, the first database may be generated through at least one of experiments with the first CT imaging system, simulations using data and models based on the first CT imaging system, or one or more analytical models using data and/or parameters based on performance characteristics of the first CT imaging system. In a similar manner, the second database may be generated through at least one of experiments with the second CT imaging system, simulations using data and models based on the second CT imaging system, or one or more analytical models using data and/or parameters based on performance characteristics of the second CT imaging system.

Accordingly, embodiments may utilize different databases of weighting factors that are based on performance characteristics of different CT imaging systems. Using the respective databases of weighting factors, a task-based IQ metric (d'gen) may be determined, as described herein, and the task-based IQ metric may be used to determine an adjusted IQ reference or an exposure-control parameter, as described herein. The second CT imaging system may then generate a TCM profile that is modified to account for differences between the first and second CT imaging systems so that image quality obtained using the first CT imaging system may be obtained using the second CT imaging system. As described above, one or more of the operations for determining the adjusted IQ reference (or the exposure-control parameter) may be performed offline and/or remotely.

In the above example, the reference system feature and the modified system feature may be, for example, a reconstruction algorithm or a scan parameter that affects radiation dose and/or image quality. Yet in other embodiments, the scan prescriptions are essentially the same (e.g., same values for the scan parameters and the same reconstruction algorithm) but the CT imaging systems are different. Accordingly, one or more embodiments may include receiving operator inputs at a current CT imaging system. The operator inputs may include a task-based input (e.g., a task-based IQ metric, a task-based IQ reference, or a target IQ reference as described herein) that represents or is related to a desired image quality for image data. The task-based input may be associated with a clinical task having a task object, wherein the image data was acquired by a reference CT imaging system. The reference CT imaging system and a current CT imaging system may be different. For example, the reference CT imaging system and the current CT imaging system may have different performances during operation.

Such embodiments may also include determining an adjusted IQ reference or an exposure-control parameter that is based on the task object, the task-based IQ metric (or target IQ reference), and at least one common system feature. The at least one common system feature may be, for example, a reconstruction algorithm or a scan parameter and help identify the database for retrieving a weighting factor. For example, a K factor may be retrieved from a database associated with the reference CT imaging system, and a K factor may be retrieved from a database associated with the current CT imaging system. The K factors may be used to determine the exposure-control parameter or the target IQ reference. A TCM profile may then be generated as described herein.

A clinical task may be limited to a region-of-interest (ROI). For example, when imaging the chest, particular clinical tasks may include detecting nodules or masses and characterizing their size and shape and relationships to organs, identifying abnormal aeration or expansion of the lungs, detect abnormal fluid collections in the chest, identify abnormal air collections both in and around the lungs, or detecting blood clots. When imaging the abdomen or pelvis, particular clinical tasks may include detecting soft tissue masses and abnormal fluid collections and determining sizes of the masses/fluid collections, identifying abnormal collections of blood, identifying air outside the intestinal tract. When imaging the head, particular clinical tasks may include detecting collections of blood, identifying brain masses, detecting brain edema or ischemia, evaluating the location of shunt hardware and the size of the ventricles, evaluating the size of the sulci and relative changes in symmetry, or detecting abnormal densities. When imaging brain perfusion, particular clinical tasks may include detecting brain ischemia (e.g., in stroke, transient ischemic attack, vasculitis), distinguishing already-infarcted brain from brain at risk of infarction, or identifying early brain tumor recurrence and higher-grade tumor components.

The above examples of clinical tasks are not limiting and additional clinical tasks exist for each ROI. Moreover, each of the above clinical tasks for chest imaging, abdomen or pelvis imaging, head imaging, and brain perfusion imaging may have a combination of qualities for the task object. For example, each of the clinical tasks may have a task object that is a function of a size, shape, and contrast. The combination of qualities may be unique for the task object of each clinical task. Alternatively, one or more task objects may have identical qualities. It is contemplated that a task object may have fewer or more qualities than those described herein.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements that do not have that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A computed tomography (CT) imaging system comprising:
    an x-ray source configured to operate at a tube current and at a tube potential while generating an x-ray beam;
    a CT detector configured to collect projection data of a person; and
    at least one processing unit configured to execute programmed instructions stored in memory, the at least one processing unit, when executing the programmed instructions, configured to:
        receive operator inputs that include a modified system feature and a clinical task having a task object;
        determine a task-based image quality (IQ) metric based on the operator inputs, the task-based IQ metric representing a desired overall image quality of image data for performing the clinical task, the image data being acquired using a reference system feature, wherein the reference system feature and the modified system feature are a same type of feature and include a reconstruction algorithm or a scan parameter;
        determine an exposure-control parameter based on the task object, the modified system feature, and the task-based IQ metric; and
        direct the x-ray source to generate the x-ray beam during a CT scan, wherein at least one of the tube current or the tube potential during the CT scan is a function of the exposure-control parameter.

2. The CT imaging system of claim 1, wherein the at least one processing unit is further configured to receive the exposure-control parameter and direct the x-ray source to generate the x-ray beam based on the exposure-control parameter.

3. The CT imaging system of claim 2, wherein the at least one processing unit is further configured to determine a tube-current modulation (TCM) profile using the exposure-control parameter, the TCM profile specifying tube currents during the CT scan for different angular and longitudinal positions of the x-ray source, wherein directing the x-ray source to generate the x-ray beam includes directing the x-ray source to generate the x-ray beam according to the TCM profile.

4. The CT imaging system of claim 1, wherein, for determining the exposure-control parameter, the at least one processing unit is further configured to:
    determine at least one weighting factor, the at least one weighting factor being based on the task object and the reconstruction algorithm; and
    calculate the exposure-control parameter using the at least one weighting factor and the task-based IQ metric.

5. The CT imaging system of claim 1, wherein the at least one processing unit is configured to direct the x-ray source to generate the x-ray beam, wherein the exposure-control parameter has a designated relationship with respect to at least one of an image noise or a radiation dose parameter, the at least one processing unit further configured to convert the exposure-control parameter to a different exposure-control parameter.

6. The CT imaging system of claim 1, wherein the at least one processing unit is configured to determine the task-based IQ metric using a detectability index, the detectability index being a task-based, frequency-dependent signal-to-noise ratio (SNR) metric that combines a spatial resolution and noise properties of the CT imaging system and a spatial-frequency content of the task object.

7. The CT imaging system of claim 1, wherein the operator inputs include a target IQ reference, the target IQ reference including at least one of a noise standard deviation or a reference tube-current product.

8. The CT imaging system of claim 1, wherein the operator inputs include a reference image having a desired overall image quality, the at least one processing unit, when executing the programmed instructions, configured to determine the task-based IQ metric using the reference image.

9. The CT imaging system of claim 8, wherein the task-based IQ metric is based on a modulation transfer function (MTF) of the CT imaging system for the clinical task, a noise power spectrum (NPS) of the CT imaging system, and a frequency content (W) of the CT imaging system for the clinical task.

10. A method comprising:
receiving operator inputs that include a modified system feature and a clinical task having a task object;
determining a task-based image quality (IQ) metric based on the operator inputs, the task-based IQ metric representing a desired overall image quality of image data for performing the clinical task, the image data being acquired using a reference system feature, wherein the reference system feature and the modified system feature are a same type of feature and include a reconstruction algorithm or a scan parameter;
determining an exposure-control parameter based on the task object, the modified system feature, and the task-based IQ metric; and
directing an x-ray source to generate an x-ray beam during a CT scan, wherein at least one of a tube current or a tube potential during the CT scan is a function of the exposure-control parameter.

11. The method of claim 10, wherein determining the exposure-control parameter includes:
determining at least one weighting factor, the at least one weighting factor being based on the task object and the reconstruction algorithm;
calculating the exposure-control parameter using the at least one weighting factor and the task-based IQ metric.

12. The method of claim 10, wherein the operator inputs include at least one of a numerical value or a reference image having a desired overall image quality, wherein the exposure-control parameter is based on the task-based IQ metric, a modulation transfer function (MTF) of a CT imaging system for the clinical task, a noise power spectrum (NPS) of the CT imaging system, and a frequency content (W) of the CT imaging system for the clinical task.

13. The method of claim 10, wherein the task-based IQ metric is obtained by a first CT imaging system, the reference system feature being used by the first CT imaging system, wherein the modified system feature is configured to be used by a second CT imaging system, wherein determining the exposure-control parameter includes determining the exposure-control parameter for the second CT imaging system.

14. A computed tomography (CT) imaging system comprising:
an x-ray source configured to operate at a tube current and at a tube potential while generating an x-ray beam;
a CT detector configured to collect projection data of a person;
at least one processing unit configured to execute programmed instructions stored in memory, the at least one processing unit, when executing the programmed instructions, configured to:
receive operator inputs that include a clinical task having a task object, a reference system feature, a modified system feature, and a target image quality (IQ) reference, the target IQ reference representing an acceptable image quality obtainable using the reference system feature, wherein the reference system feature and the modified system feature are a same type of feature and include a reconstruction algorithm or a scan parameter;
determine a task-based IQ metric based on the task object, the reference system feature, and the target IQ reference;
determine an adjusted IQ reference based on the task-based IQ metric, the task object, and the modified system feature; and
direct the x-ray source to generate the x-ray beam during a CT scan, wherein at least one of the tube current or the tube potential during the CT scan is a function of the adjusted IQ reference.

15. The CT imaging system of claim 14, wherein the at least one processing unit is further configured to receive the adjusted IQ reference and direct the x-ray source to generate the x-ray beam based on the adjusted IQ reference.

16. The CT imaging system of claim 15, wherein the at least one processing unit is further configured to determine a tube-current modulation (TCM) profile using the adjusted IQ reference, the TCM profile prescribing respective tube currents during the CT scan for different angular and longitudinal positions of the x-ray source, wherein directing the x-ray source to generate the x-ray beam includes directing the x-ray source to generate the x-ray beam according to the TCM profile.

17. The CT imaging system of claim 14, wherein the reference system feature and the modified system feature are either (a) different reconstruction algorithms or (b) different tube potentials.

18. The CT imaging system of claim 17, wherein the reconstruction algorithm of the modified system feature includes an iterative reconstruction technique.

19. The CT imaging system of claim 14, wherein the target IQ reference includes at least one of (a) a noise index representing a relative amount of noise within a medical image; (b) a reference medical image having a desired image quality; or (c) a reference mAs representing a tube current-time product divided by a spiral pitch value.

20. The CT imaging system of claim 14, wherein the adjusted IQ reference is based on a modulation transfer function (MTF), a noise power spectrum (NPS), and a frequency content (W).

\* \* \* \* \*